(12) United States Patent
Wang et al.

(10) Patent No.: US 10,202,357 B2
(45) Date of Patent: Feb. 12, 2019

(54) CLASS OF QUINOLONE HETEROCYCLIC AROMATIC MOLECULES FOR CANCER TREATMENT

(71) Applicant: RenoTarget Therapeutics, Inc., Wind Lake, WI (US)

(72) Inventors: Jujun Wang, Plano, TX (US); Allen Tsao, Wind Lake, WI (US); Xiaomei Liu, Flushing, NY (US)

(73) Assignee: RenoTarget Therapeutics, Inc., Wind Lake, WI (US)

( * ) Notice: Subject to any disclaimer, the term of this patent is extended or adjusted under 35 U.S.C. 154(b) by 0 days.

(21) Appl. No.: 15/803,478

(22) Filed: Nov. 3, 2017

(65) Prior Publication Data

US 2018/0127383 A1     May 10, 2018

Related U.S. Application Data

(60) Provisional application No. 62/419,938, filed on Nov. 9, 2016.

(51) Int. Cl.

| | |
|---|---|
| *A61K 31/517* | (2006.01) |
| *C07D 239/94* | (2006.01) |
| *A61P 35/00* | (2006.01) |
| *A61K 31/337* | (2006.01) |
| *A61K 45/06* | (2006.01) |

(52) U.S. Cl.
CPC .......... *C07D 239/94* (2013.01); *A61K 31/337* (2013.01); *A61K 31/517* (2013.01); *A61K 45/06* (2013.01); *A61P 35/00* (2018.01)

(58) Field of Classification Search
CPC .................................................. C07D 401/12
USPC ....................................... 544/242; 514/258.1
See application file for complete search history.

(56) References Cited

U.S. PATENT DOCUMENTS

| | | | |
|---|---|---|---|
| 6,897,214 | B2 | 5/2005 | Barker et al. |
| 7,879,861 | B2 | 2/2011 | Jean-Claude et al. |
| 2008/0058355 | A1 | 3/2008 | Westeim |
| 2012/0189573 | A1 | 7/2012 | Ashkenazi |

OTHER PUBLICATIONS

Zhu et al., CAS:159:699275, 2013.*
International Search Report for international application No. PCT/US2017/059997 dated Mar. 1, 2018.
Written Opinion of the International Searching Authority for international application No. PCT/US2017/059997 dated Mar. 1, 2018.

* cited by examiner

*Primary Examiner* — Rei Tsang Shiao
(74) *Attorney, Agent, or Firm* — Rodney J. Fuller; Booth Udall Fuller, PLC

(57) ABSTRACT

The invention is directed to new class of quinolone heterocyclic aromatic molecules (Renotinibs) and their use in the treatment of cancer, in particular, cancer that harbor abnormal human epidermal growth factor receptors (EGFRs).

14 Claims, 10 Drawing Sheets

CLASS OF QUINOLONE HETEROCYCLIC AROMATIC MOLECULES FOR CANCER TREATMENT

CROSS-REFERENCE TO RELATED APPLICATIONS

This application claims the benefit of U.S. Provisional Application No. 62/419,938, filed Nov. 9, 2016, the contents of which are herein expressly incorporated by reference for all purposes.

FIELD OF THE INVENTION

The invention relates to a new class of quinolone heterocyclic aromatic molecules (Renotinibs) with the core chemical structure formula below that can be used for the treatment of cancer, for example, for cancers that harbor abnormal epidermal growth factor receptors (EGFRs).

BACKGROUND OF THE INVENTION

Genome-based bioinformatics and advances in molecular sciences have considerably enriched our knowledge in understanding of the molecular mechanisms of carcinogenesis and cancer metastasis, which in turn significantly impact strategies in anticancer drug research and development. For instance, much effort has been made on developing anticancer drugs targeted at a particular cellular signal transduction pathway (one drug, one target). Consequently, several novel inhibitors have been successfully introduced into clinical practice, including inhibitors of human epidermal growth factor receptors (EGFRis).

Human EGFRs are attractive targets of cancer therapeutics owing to their abnormal expression profile in many epithelial tumors and their influence on the growth and survival of cancer cells. EGFRs are 170-180 kD transmembrane glycoproteins of the ErbB family consisting of four receptors: EGFR (HER1 or ErbB1); HER2 (neu or ErbB2); HER3 (ErbB3); and HER4 (ErbB4) (Herbst and Shin 2002; Hynes and Lane 2005). All EGFRs have an extracellular ligand-binding domain, a single membrane-spanning domain and a cytoplasmic tyrosine-kinase-containing domain (Hynes and Lane 2005). So far 10 EGFR ligands have been reported (Higashiyama, Abraham et al. 1991; Kataoka 2009). These EGFR ligands can be classified as three groups on the basis of their binding specificity to the receptors: the first consists of EGF, TGF-α and amphiregulin (AR) that are capable of binding specifically to EGFR; and the second includes β-cellulin, heparin-binding EGF (HB-EGF) and epiregulin, which show dual specificity, binding both EGFR and ErbB4. The third group is composed of the neuregulins (NRGs) and forms two subgroups on the basis of their capacity to bind ErbB3 and ErbB4 (NRG1 and NRG2) or only ErbB4 (NRG3 and NRG4) (Hynes and Lane 2005). It is of importance to note that no EGFR ligands bind to HER2 (ErbB2). However, HER2 can form heterodimers with all other members (EGFR, HER3 or HER4), and have a greater capacity for transduction of cell growth signals than homodimers, and act synergistically to promote cellular transformation (Graus-Porta, Beerli et al. 1997; Kataoka 2009). Moreover, HER2 acts independently as a major pathogenic factor in malignancy, in particular breast cancer (Hynes and MacDonald 2009).

EGFRs and their ligands are highly expressed in epithelial tumors, such as head- and neck squamous cell carcinomas, colorectal cancer, and non-small-cell lung cancer, and are important regulators of cancer cell growth, angiogenesis and metastasis. Activation of EGFRs initiates downstream signaling cascades, including those involving PI3K/Akt, Ras/Raf/mitogen-activated protein kinase (MAPK), and STAT3, thereby triggering a variety of cellular response associated with the promotion of tumor growth, proliferation, survival, angiogenesis, invasion, and metastasis (Herbst and Shin 2002; Solomon, Hagekyriakou et al. 2003; Yu and Jove 2004; Hynes and Lane 2005; Takeuchi and Ito 2010). Thus, EGFRs have become important targets for anticancer drugs. Three generations of EGFRi have been developed, and many of them have been marketed to treat local advanced or metastatic non-small cell lung cancer, recurrent or metastatic squamous cell carcinoma, or EGFR-expressing metastatic colorectal cancer. Among them Erltotinb (Tarceva) and Gefitinib (Iressa) are synthetic small molecules, whereas Cetuximab and Vectibix are humanoid monoclonal antibodies. Consequently, R&D in exploring new idea EGFRs inhibitors has been intensified (Hynes and Lane 2005; Christoffersen, Guren et al. 2009; Kataoka 2009). Most recently, FDA approved AZD9291, a third generation of EGFRi developed by AstraZeneca, that targets non-small cell lung cancer patients whose tumors share a T790M EGFR mutation (for reference, see: http://www.fiercebiotech.com/story/astrazeneca-wins-big-fast-fda-ok-az9291-lung-cancer/2015-11-13).

Like many other single-molecule-targeted chemotherapeutic drugs, EGFR inhibitors (EGFRis) are expected to have the problem of acquired resistance (Mencher and Wang 2005). Although tumors containing activating EGFR mutations (EGFRms; e.g., deletion in exon 19 or a L858R point mutation) initially respond very well to EGFRi treatment, almost all tumors will develop acquired resistance to these tyrosine kinase inhibitors (TKIs) within 9 to 15 months (Mok, Wu et al. 2009; Rosell, Carcereny et al. 2012). Various mechanisms have been identified to be involved in EGFRi acquired resistance, including acquisition of a second mutation in EGFR, e.g., T790M (a substitution of threonine at the "gatekeeper" amino acid 790 to methionine), HER2 amplification, MET Amplification, PIK3CA mutation, NF1 loss, NF1 loss, and TM4SF5-mediated epithelial-mesenchymal transition (EMT) (Kobayashi, Boggon et al. 2005; Bean, Brennan et al. 2007; Engelman, Zejnullahu et al. 2007; Lee, Kim et al. 2012; Takezawa, Pirazzoli et al. 2012; Ohashi, Sequist et al. 2012; de Bruin, Cowell et al. 2014). Among them, T790M is the most common resistance mechanism—it is detected in more than 50% tumor cells from acquired refractory patients (Kobayashi, Boggon et al. 2005). The T790M mutation is believed to render the receptor refractory to inhibition by these reversible EGFRis through exerting effects on both steric hindrance and increased ATP affinity (Yun, Mengwasser et al. 2008; Sos, Rode et al. 2010).

To overcome acquired resistance in the first generation of EGFRis, the second and third generations of EGFRis are irreversible inhibitors of EGFR and specifically target T790M. As monotherapy, the second generation of EGFRis failed to overcome T790M-mediated resistance clinically (Eskens, Mom et al. 2008; Miller, Hirsh et al. 2012; Katakami, Atagi et al. 2013), and the third generation EGFRis, such as AZD9291, acquired a new mechanism of resistance. Eberlein et al. recently reported the heterogeneous mechanisms of resistance within populations of EGFR-mutant cells (PC9 and/or NCI-H1975) to current and newly developed EGFR tyrosine kinase inhibitors, including AZD9291 (Eberlein, Stetson et al. 2015).

In addition, earlier studies showed that combination of EGFRi with standard conventional chemotherapeutic agents, such as platinum drugs did not achieve overall survival (OS) benefits (Herbst, Prager et al. 2005; Gatzemeier, Pluzanska et al. 2007).

Thus, there is a need to improve the ability of EGFRi to inhibit tumor cell growth.

SUMMARY OF THE INVENTION

In one aspect, the invention is directed to a compound having the structure of Formula I:

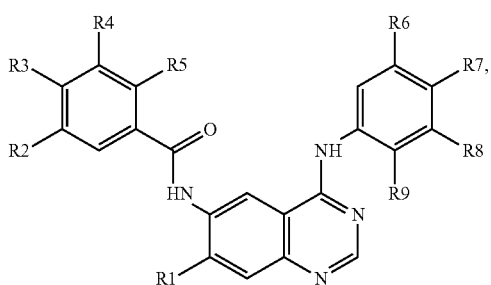

Formula I wherein: R1 is selected from the group consisting of

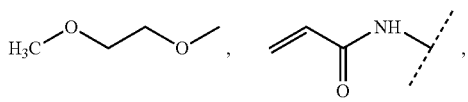

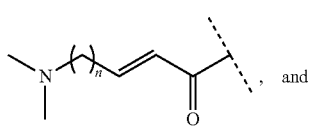, and

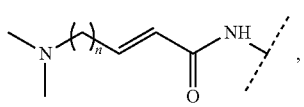, where n is 0, 1, 2, 3, or 4; R2 is selected from the group consisting of: —H, —CH₃, —OCH₃, and a halogen; R3 is selected from the group consisting of: —H, —CH₃, —OCH₃, and a halogen; R4 is selected from the group consisting of: —H, —CH₃, —OCH₃, —NO₂, and a halogen; R5 is selected from the group consisting of: —H, —CH₃, —OCH₃, and a halogen; R6 is selected from —H or a halogen; R7 is selected from —H or a halogen; R8 is selected from the group consisting of: —H, a halogen, and a ethynyl; and R9 is selected from —H or a halogen.

In some embodiments, the invention is directed to a compound having the structure of Formula II:

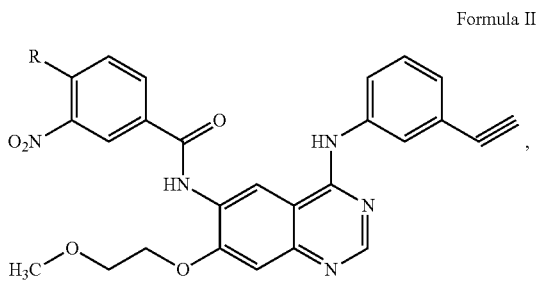

Formula II wherein R is a halogen, for example, a fluoride, a bromide, or a chloride.

In another embodiment, the invention is directed to a compound having the structure of Formula III:

Formula III wherein R is a halogen, for example, a fluoride, a chloride, a bromide, or a iodide.

The invention also encompasses methods of synthesizing the compound of Formula II.

In another aspect, the invention is directed to pharmaceutical composition comprising a compound of the present invention, for example a composition comprising a compound having the structure of Formula I, Formula II, Formula III, or Formula IV and at least one anti-cancer agent. The anti-cancer agent may be selected from the group consisting of: a conventional chemotherapeutic agent, a protein kinase inhibitor, a topoisomerase inhibitor, a mitotic kinesin inhibitor, a histone deacetylase inhibitor, a mTOR inhibitor, a growth factor inhibitor, a growth factor receptor inhibitor, a transcriptional factor inhibitor, an anticancer monoclonal antibody, and glucocorticoid hormones.

The invention is also directed to methods for inhibiting proliferation of a cell having abnormal EGFR activity comprising administering to the cell having abnormal EGFR activity a compound of the present invention. In some implementations, the methods further comprise administering at least one anti-cancer agent selected from the group consisting of: a conventional chemotherapeutic agent, a protein kinase inhibitor, a topoisomerase inhibitor, a mitotic kinesin inhibitor, a histone deacetylase inhibitor, a mTOR inhibitor, a growth factor inhibitor, a growth factor receptor inhibitor, a transcriptional factor inhibitor, an anti-cancer monoclonal antibody, and glucocorticoid hormones.

In some embodiments, the at least one anti-cancer agent is paclitaxel or its derivatives. In such embodiments, the

DETAILED DESCRIPTION

Figure 1:
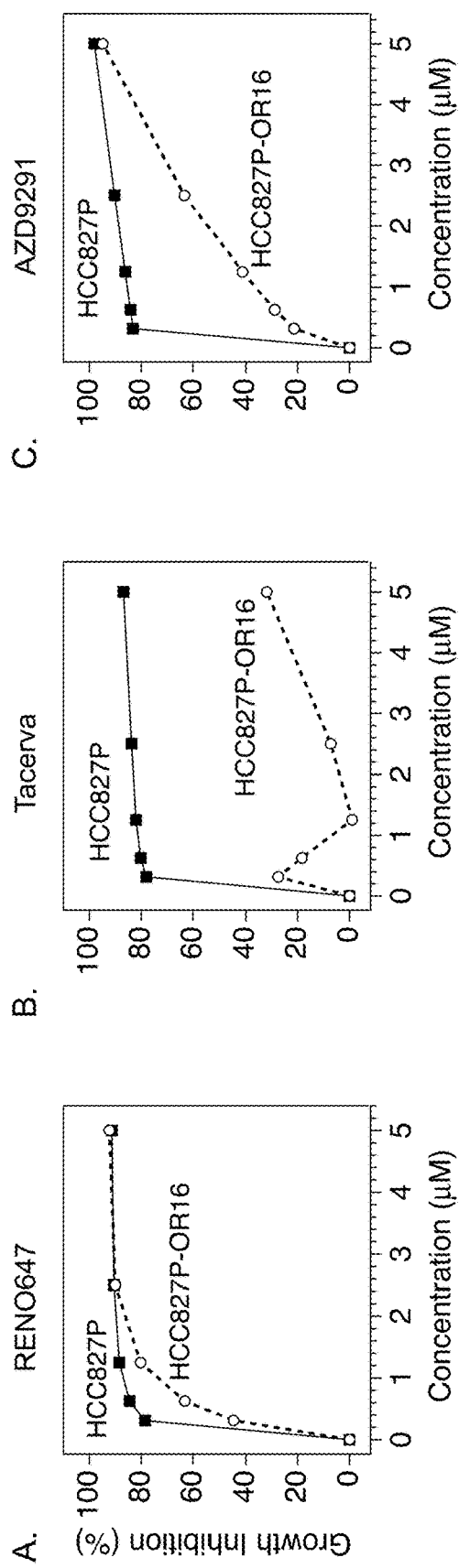
FIG. 1 depicts the effect of Reno647 (panel A), Tarceva (a first generation EGFRi, panel B), and AZD9291 (a third generation EGFRi, panel C) on growth inhibition of HCC827 and its AZD9291-resistant cell line HCC8270R16. Cells grown exponentially were aliquoted into 96-well plates at a density of 3,000 cells/200 µl per well in RPMI 1640 medium containing 10% FBS. After 24 hrs of incubation, cells were exposed to the indicated concentrations of tested compounds for 72 hrs. Cell growth was then measured by SRB method as described in the section of Example 2.1. Mean, standard deviation (SD), and the percent of growth inhibition at each concentration point of the treatment were calculated. Percent of growth inhibition is defined as (1-T/C)×100, where T is the mean of the absorbance at 570 nm from the treatment and C from control (drug vehicle only).

This invention is based on the idea that cells given cancer drugs targeting more than one pathway have less chance to develop drug resistance (Mencher and Wang 2005). Poly (ADP-ribose) polymerase (PARP) is a family of proteins involved in mainly DNA repair and programmed cell death. In the past few years PARP inhibitors have been moved from the laboratory to the clinic trials for treating cancers. Recent studies have showed that PARP inhibitors suppress EGFR mutated cancer cell growth through targeting nuclear PKM2, and some EGFR-resistant-lung cancers are sensitive to PARP inhibitors (Li, Feng et al. 2016). Thus, to overcome these existing issues of EGFRi, a new class of inhibitors against dual targets of cancer cells are developed by fusing EGFRi with Poly (ADP-ribose) polymerase inhibitors (PARPi). Accordingly, the new class of quinolone heterocyclic aromatic molecules, also referred to "Renotinibs," can be used as therapeutic agents in the treatment of various types of cancers, for example, for the cancers that harbor abnormal EGFRs, including human EGFRs. As used herein, "abnormal EGFR" refers to a mutated or truncated EGFR. "Abnormal EGFR" may also refer to an EGFR with a downstream pathway that is dysfunctional in its activity (for example, it is constitutively active). As used herein, "treatment" refers to any improvement in the clinical symptoms of the cancer, as well as any improvement in the well being of the patients, in particular an improvement manifested by at least one of the following: decrease in tumor size, decrease in serum/plasma biomarkers, and prevention of tumor progression or metastasis. In one embodiment, this is accomplished by administering an amount of "Renotinibs" sufficient to inhibit mutated EGFR activity, induce p21 expression, promote cancer cell apoptosis, and/or block cancer migration and invasion.

In some embodiments, the EGFRi portion of the Renotinib is based on Tarceva (a first generation of EGFRi) while the PARP inhibitor portion is based on BSI-201, a PARPi targeting both the NI-subsite and AD-subsite (Qiu, Lam et al. 2014). In some aspects, the Renotinibs have the structure of Formula I:

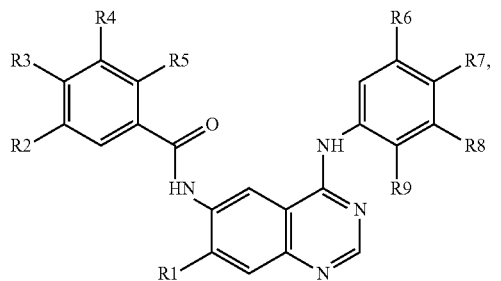

Formula I wherein: R1 is selected from the group consisting of:

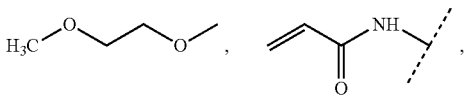

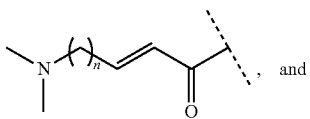, and

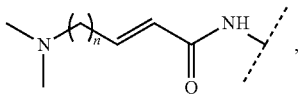, where n is 0, 1, 2, 3, or 4;

R2 is selected from the group consisting of: —H, —CH$_3$, —OCH$_3$, and a halogen;

R3 is selected from the group consisting of: —H, —CH$_3$, —OCH$_3$, and a halogen;

R4 is selected from the group consisting of: —H, —CH$_3$, —OCH$_3$, —NO$_2$, and a halogen;

R5 is selected from the group consisting of: —H, —CH$_3$, —OCH$_3$, and a halogen;

R6 is selected from —H or a halogen;

R7 is selected from —H or a halogen;

R8 is selected from the group consisting of: —H, a halogen, and a ethynyl; and

R9 is selected from —H or a halogen.

In one embodiment, the Renotinib has the structure of Formula II:

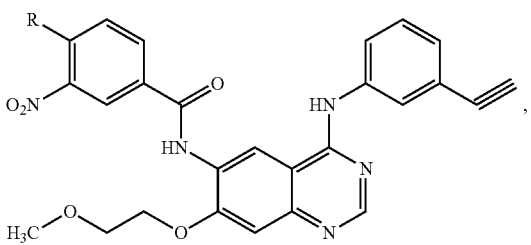

Formula II wherein R is a halogen. Preferably, R is selected from the group consisting of: fluoride, chloride, and bromide. In a most preferred embodiment, R is a fluoride.

In another embodiment, the Renotinib has the structure of Formula III:

Formula III

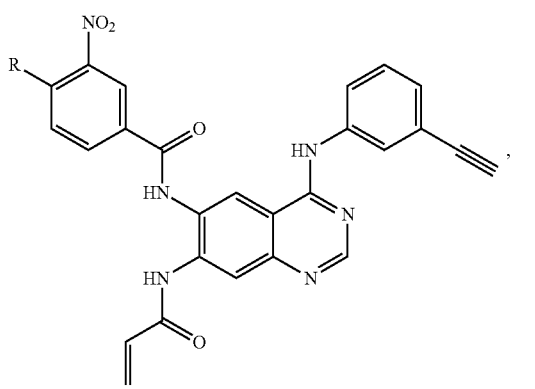

wherein R is a halogen, for example, R is fluoride, chloride, bromide, or iodide.

In some aspects of the invention the disclosed compound is in the form of a pharmaceutically acceptable salt. Exemplary salts include sodium, potassium, calcium, magnesium, ammonium, and tetraalkylammonium. Pharmaceutically acceptable salts also include any salt derived from an organic or inorganic acid. Examples of such salts made with inorganic salt include but are not limited to the following: salts of hydrobromic acid, hydrochloric acid, nitric acid, phosphoric acid, and sulfuric acid. Examples of such salts made with organic acids include but are not limited to the following: salts of acetic acid, propionic acid, hexanoic acid, benzenesulfonic acid, benzoic acid, tertiary butylacetic acid camphorsulfonic acid, cinnamic acid, citric acid, 4-chlorobenzenesulfonic acid, 2-(4-chlorophenoxy)-2-methylpropionic acid, cyclopentanepropionic acid, n-dodecyl sulphuric acid, 1,2-ethanedisulfonic acid, ethanesulfonic acid, ethylenediaminetetraacetic acid (EDTA), fumaric acid, glucoheptonic acid, gluconic acid, glutamic acid, glycolic acid, N-glycolylarsanilic acid, 4-hexylresorcinol, hippuric acid, 2-(4-hydroxybenzoyl)benzoic acid, 1-hydroxy-2-naphthoic acid, 3-hydroxy-2-naphthoic acid, 2-hydroxyethanesulphonic acid, lactic acid, lactobionic acid, lauryl sulfuric acid, maleic acid, malic acid, mandelic acid, malonic acid, methanesulfonic acid, 4-methylbicyclo[2.2.2]-oct-2-ene-1-carboxylic acid, methyl sulfuric acid, muconic acid, 2-naphthalenesulphonic acid, oxalic acid, pamoic acid, pantothenic acid, 3-phenylpropionic acid, phosphanilic acid ((4-aminophenyl) phosphonic acid), picric acid, salicylic acid, stearic acid, succinic acid, tannic acid, tartaric acid, terephthalic acid, trimethylacetic acid, p-toluenesulfonic acid, 10-undecenoic acid, or any other such acid now known or yet to be disclosed. Pharmaceutically acceptable salts also includes salts formed when an acidic proton present in the parent compound is either replaced by a metal ion, e.g., an alkali metal ion, an alkaline earth metal ion, an aluminum ion, or coordinates with an organic base such as ethanolamine, diethanolamine, triethanolamine, trimethylamine, N-methylglucamine, and the like. Suitable salts further include those described in P. Heinrich Stahl, Camille G. Wermuth (Eds.), Handbook of Pharmaceutical Salts Properties, Selection, and Use (2002).

It will be appreciated by one skilled in the art that such pharmaceutically acceptable salts may be used in the formulation of a pharmacological composition. Such salts may be prepared by reacting the disclosed compound with a suitable acid in a manner known by those skilled in the art.

Pharmaceutical Compositions and Dosage Forms

The invention is also directed to pharmaceutical compositions comprising a Renotinib. In some aspects, the pharmaceutical composition comprises a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, such as binder, surfactant, and lubricant, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used. In a preferred embodiment, the pharmaceutically acceptable carrier is an inert diluent.

In one embodiment, the pharmaceutical composition may further comprise one or more anti-cancer agents. The anti-cancer agent can be any agent useful in treating cancer. Preferably the anticancer agent is a conventional chemotherapeutic agent (such as an alkylating agent, an anti-metabolitic agent, an antibiotic, an anti-tubule agents, or an anti-hormonal agents), a protein kinase inhibitor (including, but not limited to an inhibitor of cyclin-dependent kinases, tyrosine kinases, phosphoinositide 3-kinase PI3K/AKT, protein kinase C, casein kinases, MAP kinases, or Src kinases), a topoisomerase inhibitor, a mitotic kinesin inhibitor, a histone deacetylase inhibitor, a mTOR inhibitor, a growth factor inhibitor, a growth factor receptor inhibitor, a transcriptional factor inhibitor, an anticancer monoclonal antibody, or a glucocorticoid hormone.

Examples of preferred conventional chemotherapeutic agent include, but are not limited to mechlorethamine (Embichin), cyclophosphamide (Endoxan), Myleran (Busulfan), chlorambucil, leukeran, paraplatin, cisplatin, carboplatin, platinol, Methotrexate (MTX), 6-mercaptopurine (6-MP), cytarabine (Ara-C), floxuridine (FUDR), fluorouracil (Adrucil), hydroxyurea (Hydrea), etoposide (VP16), actinomycin D, bleomycin, mithramycin, daunorubicin, taxol and its derivatives, vinca and its derivatives, bicalutamide (Casodex), Flutamide (Eulixin), Tamoxifen (Noluadex), Megestrol (Magace), and combinations thereof.

Examples of preferred a protein kinase inhibitor include midostaurin (PKC-412, CGP 41251, N-benzoylstaurosporine), UCN-01 (7-hydroxystaurosporine), bryostatin 1, perifosine, ilmofosine, Ro 31-8220, Ro 32-0432, GO 6976, ISIS-3521 (CGP 64128A) and the macrocyclic bis (indolyl) maleimides (LY-333531, LY-379196, LY-317615), AZD9291, Tarceva as well as others under development, and combinations thereof.

Examples of a preferred anticancer monoclonal antibody include, but not limited to Cetuximab (Erbitux), Herceptin, Bevacizumab (Avastin), and combinations thereof.

Examples of preferred glucocorticoid hormones include, but are not limited to dexamethasone, prednisone, prednisolone, metyylprednisolone, and hydrocoritisone.

The pharmaceutical compositions of the invention can take a variety of forms adapted to the chosen route of administration as discussed above. Those skilled in the art will recognize various synthetic methodologies that may be employed to prepare non-toxic pharmaceutically acceptable compositions of the compounds described herein. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide (DMSO).

Pharmaceutical compositions can be used in the preparation of individual dosage forms. Consequently, pharmaceutical compositions and dosage forms of the invention comprise the active ingredients disclosed herein. The notation of "the compound" signifies the compounds of the invention described herein or salts thereof.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; pills, caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their route of administration and the mammal animal being treated. For example, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

For a particular condition or method of treatment, the dosage is determined empirically, using known methods, and will depend upon facts such as the biological activity of the particular compound employed, the means of administrations, the age, health and body weight of the host, the nature and extent of the symptoms, the frequency of treatment, the administration of other therapies, and the effect desired. Hereinafter are described various possible dosages and methods of administration with the understanding that the following are intended to be illustrative only. The actual dosages and the method of administration or delivery may be determined by one of skill in the art.

Dosage levels of the order are from about 0.01 mg to about 50 mg per kilogram of body weight per day, more preferably from about 0.25 mg to about 10 mg per kilogram of body weight per day, and even more preferably between 10 mg to about 200 mg per kilogram of body weight per day are useful in the treatment of cancer in humans. Dosage unit forms will generally contain between from about 5 mg to about 100 mg per kilogram of body weight per day of the compound for humans.

For illustrative purposes, dosage levels of the administered active ingredients in animals may be: intravenous, 0.01 to about 50 mg/kg; intramuscular, 0.05 to about 50 mg/kg; orally, 0.5 to about 150 mg/kg; intranasal instillation, 0.5 to about 10 mg/kg; and aerosol, 0.5 to about 100 mg/kg of host body weight. The dose level is usually about 10 times less in human than in other animals.

Frequency of dosage may also vary depending on the compound used and whether an extended release formulation is used. However, in a preferred embodiment, the treatment of human cancer is 3 times daily or less.

Preferably the compound is administered to the cancer patients for a period of at least 16 weeks (4 weeks a cycle for 4 cycles). Applicants have discovered benefits of continuous extended administration of the compound to the cancer patients being treated. In certain embodiments, administration may be for at least six months, at least a year or even longer. For most cancer conditions, the treatment should continue until disease progression or unacceptable toxicity occurs.

In another preferred embodiment, Renotinibs can also be used in combination with other therapies, including but not limited to surgery, radiation, or gene therapy.

1. Oral Dosage Forms

Pharmaceutical compositions of the invention that are suitable for oral administration can be presented as discrete dosage forms, such as, but are not limited to, tablets (e.g., chewable tablets), pills, caplets, capsules, and liquids (e.g., flavored syrups). Such dosage forms contain predetermined amounts of active ingredients, and may be prepared by methods of pharmacy well known to those skilled in the art.

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, Natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103.™, and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an active ingredient, anhydrous lactose, microcrystalline cellulose, polyvinylpyrrolidone, stearic acid, colloidal anhydrous silica, and gelatin.

2. Controlled Release Dosage Forms

Active ingredients of the invention can be administered by controlled release means or by delivery devices that are well known to those of ordinary skill in the art. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

3. Parenteral Dosage Forms

Parenteral dosage forms can be administered to patients by various routes including, but not limited to, subcutaneous, intravenous, bolus injection, intramuscular, and intraarterial. Because their administration typically bypasses patients' Natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Methods of Use

In another aspect, the invention is directed to methods of using Renotinibs. One method is in the treatment of cancer and proliferative related diseases, namely inhibiting cell growth of a cell having abnormal EGFR activity comprising administering to the cell having abnormal EGFR activity a compound having the structure of Formula I, Formula II, or Formula III. In some embodiments, the method further comprises administering at least one anti-cancer agent selected from the group consisting of: a conventional chemotherapeutic agent, a protein kinase inhibitor, a topoisomerase inhibitor, a mitotic kinesin inhibitor, a histone deacetylase inhibitor, a mTOR inhibitor, a growth factor inhibitor, a growth factor receptor inhibitor, a transcriptional factor inhibitor, an anticancer monoclonal antibody, or glucocorticoid hormones.

The conventional chemotherapeutic agent is selected from group consisting of: an alkylating agent, an antimetabolitic agent, an antibiotic, an anti-tubule agent, and an anti-hormonal agent. For example, the conventional chemotherapeutic agent is selected from the group consisting of: mechlorethamine, cyclophosphamide, Busulfan, chlorambucil, leukeran, paraplatin, cisplatin, carboplatin, platinol, Methotrexate (MTX), 6-mercaptopurine (6-MP), cytarabine (Ara-C), floxuridine (FUDR), fluorouracil, hydroxyurea (Hydrea), etoposide (VP16), camptothecin, camptothecin derivatives, actinomycin D, bleomycin, mithramycin, daunorubicin, taxol and its derivatives, vinca and its derivatives, bicalutamide, Flutamide, Tamoxifen, and Megestrol.

The protein kinase inhibitors include inhibitors of cyclin-dependent kinases, tyrosine kinases, phosphoinositide 3-kinase PI3K/AKT, protein kinase C, casein kinases, MAP kinases, and Src kinases. For example, the protein kinase inhibitor is selected from the group consisting of: midostaurin, 7-hydroxystaurosporine, bryostatin 1, perifosine, ilmofosine, Ro 31-8220, Ro 32-0432, GO 6976, ISIS-3521, macrocyclic bis (indolyl) maleimides, AZD9291, and erlotinib.

The anticancer monoclonal antibody is selected from the group consisting of: Cetuximab, Herceptin, and Bevacizumab.

The glucocorticoid hormone is selected from the group consisting of: dexamethasone, prednisone, prednisolone, metyylprednisolone, and hydrocoritisone.

The at least one anti-cancer agent may be administered concurrently with Renotinib or separately in different treatment periods. For administration of the at least one anti-cancer agent and Renotinib in separate treatment periods, the at least one anti-cancer agent is administered for the first treatment period before Renotinib is administered, or Renotinib is administered for the first treatment period before at least one anti-cancer agent is administered. When multiple anti-cancer agents are administered in the method, Renotinib may be administered in separate treatment periods from all of the anti-cancer agents or administered in separate treatment periods from only some of the anti-cancer agents.

In some embodiments, the at least one anti-cancer agent is paclitaxel or its derivatives. In one implementation, the method comprises administering the compound of Formula I and paclitaxel or its derivatives concurrently. In another implementation, the method comprises administering paclitaxel or its derivatives for a treatment period before administering the compound of Formula I.

EXAMPLES

The present invention will now be illustrated by the following non-limiting examples. It is to be understood that the foregoing describes preferred embodiments of the present invention and that modifications may be made therein without departing from the spirit or scope of the present invention as set forth in the claims.

1. Chemistry

General Methods: $^1$H NMR spectra were recorded on a Varian Inova 300 or 500 MHz NMR instrument. Chromatographic purities were determined on an Agilent 1200 Series or 1100 Series LC/MS system using a Merck Chromolith RP-18e analytical HPLC column (monolithic, 50×2 mm) and the following analytical HPLC method: injection volume 5 µL; flow rate 1 mL/min; 5→95% acetonitrile in water over 5 mins; Agilent diode array detector at λ=254 or 220 nm; room temperature.

Synthetic Scheme for Quinazoline Derivatives:

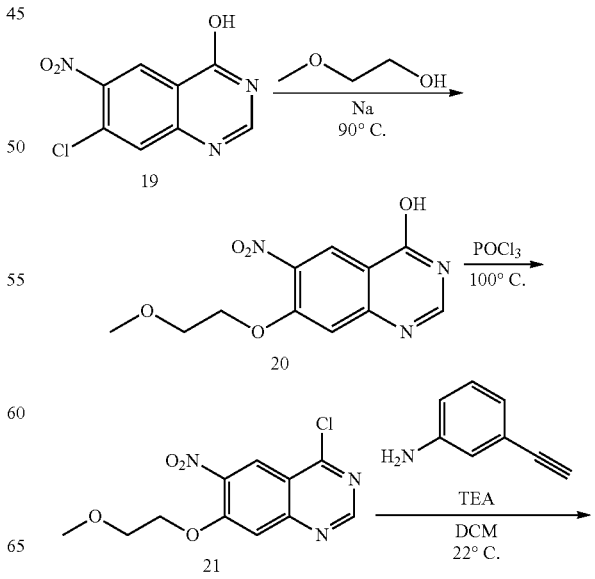

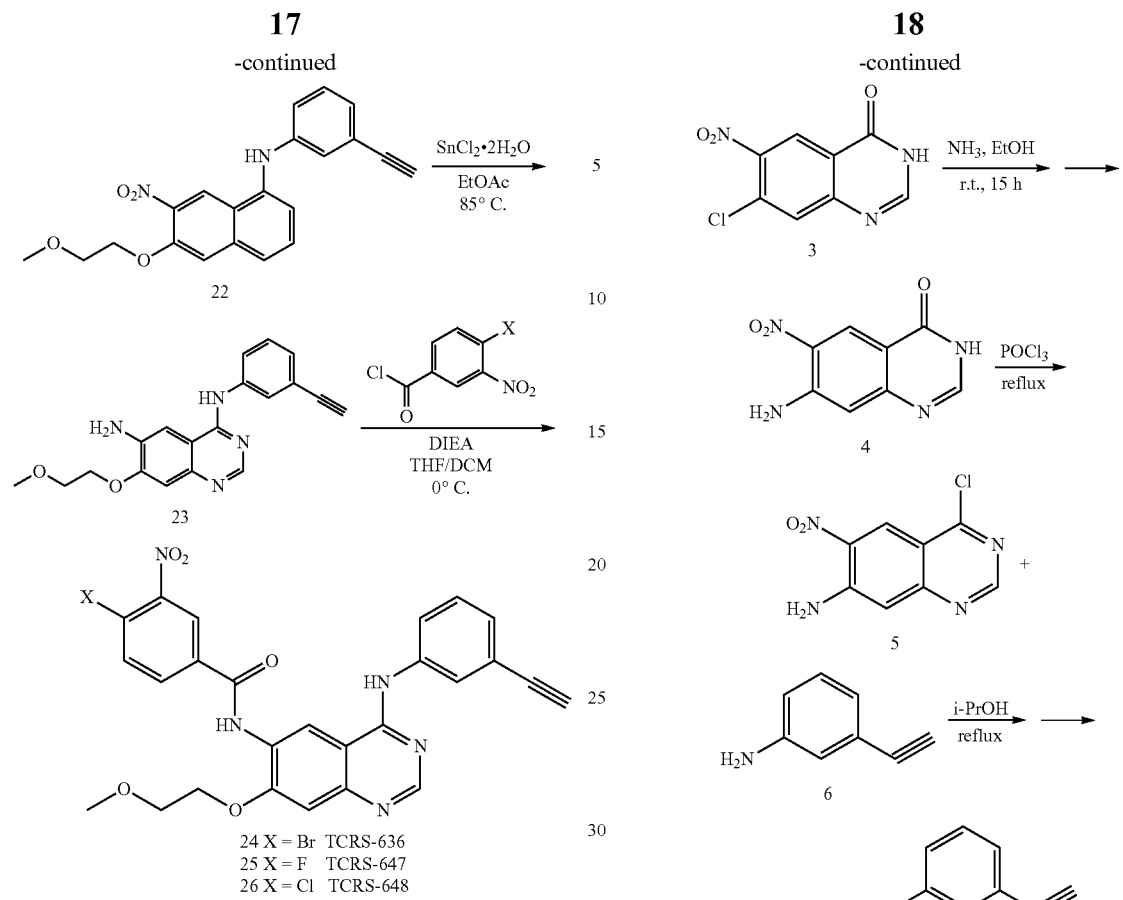
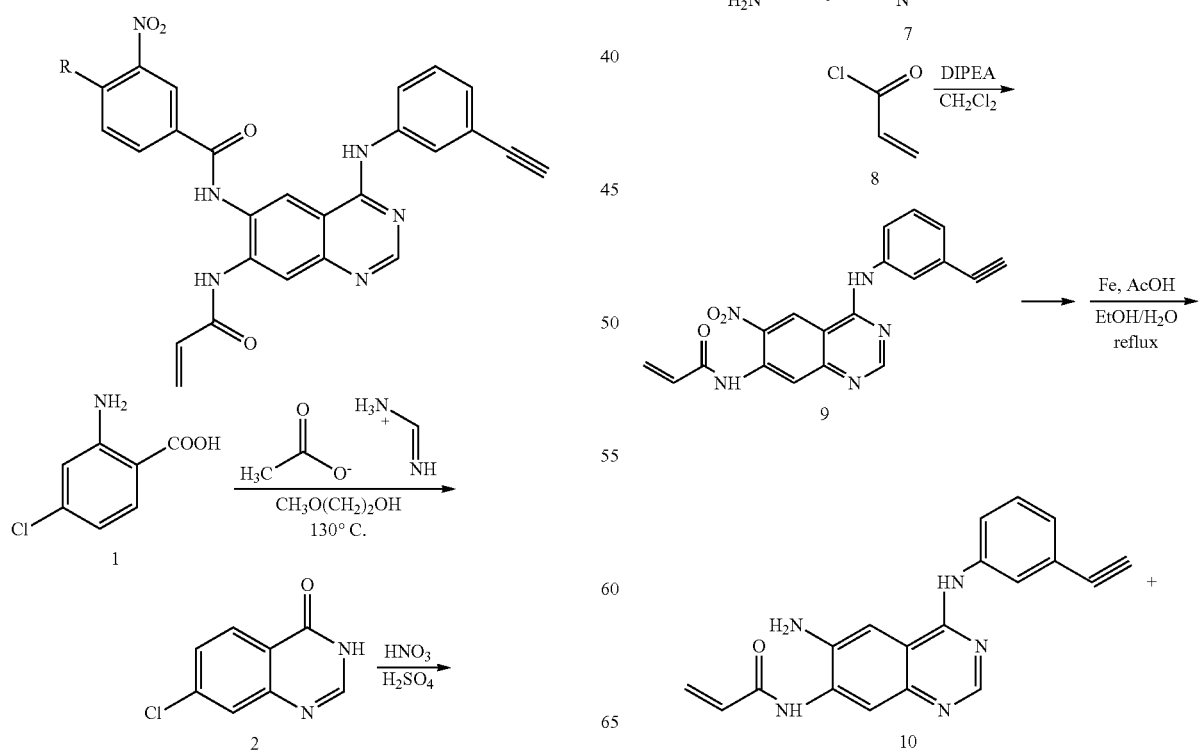
Synthetic Scheme for Formula III

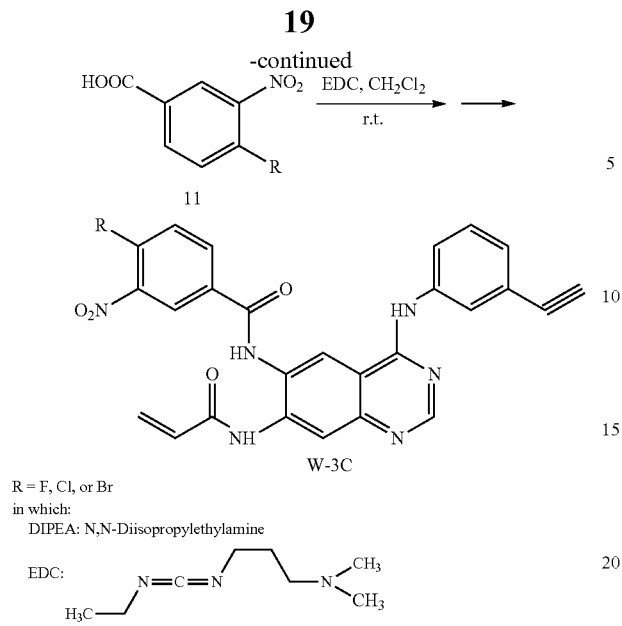

R = F, Cl, or Br
in which:
DIPEA: N,N-Diisopropylethylamine

EDC:

1.2 Preparation of 7-(2-Methoxy-ethoxy)-6-nitro-quinazolin-4-ol (20)

To an Ar purged flask of 2-methoxy-ethanol (43 mL), under Ar, added sodium metal (532 mg, 22.2 mmol). The mixture was stirred at 22° C. until the sodium metal dissolved (~45 min), at which time 7-chloro-6-nitro-quinazolin-4-ol (2.50 g, 11.1 mmol) was added. The resulting mixture was stirred at 90° C. for 40 h. The reaction was concentrated in vacuo, dissolved in H$_2$O (250 mL) and extracted with DCM (1×50 mL). The aqueous layer was then acidified with 1N HCl to pH=1. Extracted with DCM (1×100 mL), CHCl$_3$ (2×100 mL) and THF (1×100 mL). The combined organics were dried over MgSO$_4$, filtered and concentrated. The aqueous layer was partially concentrated in vacuo and lyophilized. Both residues were combined and the product was isolated via column chromatography in 0→10% MeOH in DCM to afford the desired product (20) as a yellow solid (2.6 g, 88% yield, 9.75 mmol).

LC/MS: retention time 1.90 min
(ES+) calc for C$_{11}$H$_{12}$N$_3$O$_5$: [M+H]+266; found 266.

1.3 Preparation of 4-Chloro-7-(2-methoxy-ethoxy)-6-nitro-quinazoline (21)

To an Ar purged flask of 7-(2-methoxy-ethoxy)-6-nitro-quinazolin-4-ol (20) (1.0 g, 3.77 mmol), added POCl$_3$ (9.4 mL). The mixture was refluxed at 100° C. for 55 h at which time the reaction was judged complete. The reaction was concentrated in vacuo, dissolved in EtOAc (250 mL) and washed with H$_2$O (2×100 mL), sat. NaHCO$_3$ (aq) (2×100 mL) and brine (1×100 mL). The organics were dried over MgSO$_4$, filtered and concentrated. The residue was purified via column chromatography in 0→100% EtOAc in Hexanes to afford the desired product (21) as yellow solid (856 mg, 73% yield, 3.02 mmol).

LC/MS: retention time 2.55 min
(ES+) calc for C$_{11}$H$_{10}$ClN$_3$O$_4$: [M+H]+284; found 284.

1.4 Preparation of (3-Ethynyl-phenyl)-[6-(2-methoxy-ethoxy)-7-nitro-naphthalen-1-yl]-amine (22)

To a solution of 4-chloro-7-(2-methoxy-ethoxy)-6-nitro-quinazoline (21) (225 mg, 0.793 mmol) in isopropanol (4.0 mL), added 3-ethynyl-phenylamine (147 µL, 0.872 mmol) and triethylamine (96.3 µL, 0.691 mmol). The mixture was refluxed at 83° C. for 3 h. The reaction was cooled to 22° C., the formed ppt was collected and washed with H$_2$O. The residue was purified via column chromatography in 0→10% MeOH in DCM to afford the desired product (22) as yellow solid (266 mg, 92% yield, 0.730 mmol).

LC/MS: retention time 2.73 min
(ES+) calc for C$_{19}$H$_{17}$N$_4$O$_4$: [M+H]+365; found 365.

1.5 Preparation of N$^4$-(3-Ethynyl-phenyl)-7-(2-methoxy-ethoxy)-quinazoline-4,6-diamine (23)

To a solution of (3-ethynyl-phenyl)-[6-(2-methoxy-ethoxy)-7-nitro-naphthalen-1-yl]-amine (22) (142 mg, 0.390 mmol), in EtOAc (13.0 mL), was added SnCl$_2$.2H$_2$O (396 mg, 1.75 mmol). The resulting mixture was refluxed at 85° C. for 2 h. The reaction was cooled to 22° C., then H$_2$O (5 mL) was added, followed by sat. NaHCO$_3$ (aq) (~20 mL) until pH 9-10. The mixture was extracted with EtOAc (3×20 mL) and the combined organics were washed with brine (1×20 mL) and H$_2$O (1×20 mL). The organics were dried over MgSO$_4$, filtered and concentrated. The residue was purified via column chromatography in 0→15% MeOH in DCM to afford the desired product (23) as a light yellow solid (75.6 mg, 58% yield, 0.226 mmol).

LC/MS: retention time 1.85 min
(ES+) calc for C$_{19}$H$_{19}$N$_4$O$_2$: [M+H]+335; found 335.

1.6 Preparation of 4-Bromo-N-[4-(3-ethynyl-phenylamino)-7-(2-methoxy-ethoxy)-quinazolin-6-yl]-3-nitro-benzamide (24) (Reno636)

To an Ar purged solution of 4-bromo-3-nitro-benzoic acid (25.0 mg, 0.102 mmol) in DCM (1.0 mL) added oxalyl chloride (17 µL, 0.204 mmol), followed by DMF (1 drop) at 22° C. After 30 minutes, the conversion to the acid chloride was confirmed by treating a small aliquot of the reaction mixture with MeOH and observing the resulting methyl ester by LC/MS. The reaction was concentrated and DCM (1.0 mL) was added to make a stock solution of the crude acid chloride.

To an Ar purged solution of N4-(3-ethynyl-phenyl)-7-(2-methoxy-ethoxy)-quinazoline-4,6-diamine (23) (26.0 mg, 0.0778 mmol) in THF (1.0 mL) at 0° C. (ice/brine bath), added DIEA (34 µL, 0.195 mmol) and 4-bromo-3-nitro-benzoyl chloride (0.90 mL of the freshly prepared solution above, 0.0855 mmol). The resulting mixture was allowed to stir at 22° C. for 45 min. The mixture was diluted with DCM and CHCl$_3$ (10 mL total) and washed with sat. NH$_4$Cl (aq) (1×10 mL), sat. NaHCO$_3$ (aq) (2×10 mL) and brine (1×10 mL). The organics were dried over MgSO$_4$, filtered and concentrated. The residue was purified via reverse phase column chromatography (5→95% MeCN in H$_2$O, each containing 0.05% AcOH) and desired fractions were lyophilized. A second column chromatography in 0→10% MeOH in DCM afforded the desired product (24) as a yellow crystalline solid (21.6 mg, 49%, 0.0384 mmol).

LC/MS: retention time 2.82 min
(ES+) calc for C$_{26}$H$_{21}$BrN$_5$O$_5$: [M+H]+562, 564; found 562, 564.

1.7 Preparation of 4-Fluoro-N-[4-(3-ethynyl-phenylamino)-7-(2-methoxy-ethoxy)-quinazolin-6-yl]-3-nitro-benzamide (25) (Reno647)

To an Ar purged solution of 4-fluoro-3-nitro-benzoic acid (50.0 mg, 0.270 mmol) in DCM (1.5 mL) added oxalyl chloride (46 μL, 0.540 mmol), followed by DMF (1 drop) at 22° C. After 30 minutes, the conversion to the acid chloride was confirmed by treating a small aliquot of the reaction mixture with MeOH and observing the resulting methyl ester by LC/MS. The reaction was concentrated and DCM (1.0 mL) was added to make a stock solution of the crude acid chloride.

To an Ar purged solution of N4-(3-ethynyl-phenyl)-7-(2-methoxy-ethoxy)-quinazoline-4,6-diamine (23) (25.0 mg, 0.0748 mmol) in THF (1.0 mL) at 0° C. (ice/brine bath), added DMA (33 μL, 0.187 mmol) and 4-fluoro-3-nitro-benzoyl chloride (0.30 mL of the freshly prepared solution above, 0.0822 mmol). The resulting mixture was allowed to stir at 22° C. for 60 min. The mixture was diluted with DCM and CHCl₃ (10 mL total) and washed with sat. NH₄Cl (aq) (1×10 mL), sat. NaHCO₃ (aq) (2×10 mL) and brine (1×10 mL). The organics were dried over MgSO₄, filtered and concentrated. The residue was purified via reverse phase column chromatography (5→95% MeCN in H₂O, each containing 0.05% AcOH) and desired fractions were lyophilized to afford the desired product (25) as a yellow crystalline solid (11.8 mg, 32%, 0.0235 mmol).

LC/MS: retention time 2.75 min (ES+) calc for $C_{26}H_{21}FN_5O_5$: [M+H]+502; found 502.

Formula IV provides the structure of Reno647:

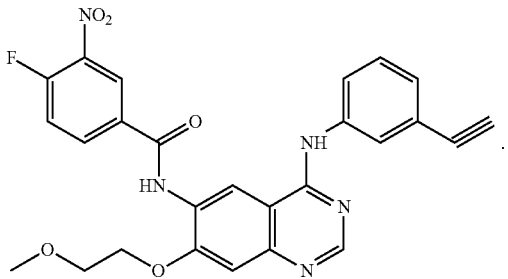

Formula IV 1.8 Preparation of 4-Chloro-N-[4-(3-ethynyl-phenylamino)-7-(2-methoxy-ethoxy)-quinazolin-6-yl]-3-nitro-benzamide (26) (Reno648)

To an Ar purged solution of 4-fluoro-3-nitro-benzoic acid (50.0 mg, 0.248 mmol) in DCM (1.25 mL) added oxalyl chloride (42 μL, 0.496 mmol), followed by DMF (1 drop) at 22° C. After 30 minutes, the conversion to the acid chloride was confirmed by treating a small aliquot of the reaction mixture with MeOH and observing the resulting methyl ester by LC/MS. The reaction was concentrated and DCM (1.0 mL) was added to make a stock solution of the crude acid chloride.

To an Ar purged solution of N4-(3-ethynyl-phenyl)-7-(2-methoxy-ethoxy)-quinazoline-4,6-diamine (23) (25.0 mg, 0.0748 mmol) in THF (1.0 mL) at 0° C. (ice/brine bath), was added DIEA (33 μL, 0.187 mmol) and 4-chloro-3-nitro-benzoyl chloride (0.33 mL of the freshly prepared solution above, 0.0822 mmol). The resulting mixture was allowed to stir at 22° C. for 60 min. The mixture was diluted with DCM and CHCl₃ (10 mL total) and washed with sat. NH₄Cl (aq) (1×10 mL), sat. NaHCO₃ (aq) (2×10 mL) and brine (1×10 mL). The organics were dried over MgSO₄, filtered and concentrated. The residue was purified via reverse phase column chromatography (5→0.95% MeCN in H₂O, each containing 0.05% AcOH) and desired fractions were lyophilized to afford the desired product (26) as a yellow crystalline solid (6.2 mg, 16%, 0.0120 mmol).

LC/MS: retention time 2.89 min (ES+) calc for $C_{26}H_{21}ClN_5O_5$: [M+H]+518; found 518.

1.9 Preparation of 4-Iodo-N-[4-(3-ethynyl-phenylamino)-7-(2-methoxy-ethoxy)-quinazolin-6-yl]-3-nitro-benzamide (27) (Reno649)

To an Ar purged solution of 4-iodo-3-nitro-benzoic acid (50.0 mg, 0.171 mmol) in DCM (1.0 mL) added oxalyl chloride (29 μL, 0.341 mmol), followed by DMF (1 drop) at 22° C. After 30 minutes, the conversion to the acid chloride was confirmed by treating a small aliquot of the reaction mixture with MeOH and observing the resulting methyl ester by LC/MS. The reaction was concentrated and DCM (1.0 mL) was added to make a stock solution of the crude acid chloride.

To an Ar purged solution of N4-(3-ethynyl-phenyl)-7-(2-methoxy-ethoxy)-quinazoline-4,6-diamine (23) (25.0 mg, 0.0748 mmol) in THF (1.0 mL) at 0° C. (ice/brine bath), added DIEA (33 μL, 0.187 mmol) and 4-iodo-3-nitro-benzoyl chloride (0.48 mL of the freshly prepared solution above, 0.0822 mmol). The resulting mixture was allowed to stir at 22° C. for 60 min. The mixture was diluted with DCM and CHCl3 (10 mL total) and washed with sat. NH₄Cl (aq) (1×10 mL), sat. NaHCO₃ (aq) (2×10 mL) and brine (1×10 mL). The organics were dried over MgSO₄, filtered and concentrated. The residue was purified via reverse phase column chromatography (5→95% MeCN in H₂O, each containing 0.05% AcOH) and desired fractions were lyophilized to afford the desired product (27) as a yellow crystalline solid (16.4 mg, 36%, 0.0269 mmol).

LC/MS: retention time 2.97 min (ES+) calc for $C_{26}H_{21}IN_5O_5$: [M+H]+610; found 610.

2. Effects on Cancer Cell Proliferation 2.1 Inhibition of Tested Compounds on Cancer Cell Growth Compounds:

All compounds tested in this section were synthesized as described in Example 1, and structured characterized by NM, MS, and purified by HPLC with a purity ≥98.0%.

Reagents:

Tarceva and AZD9291 were purchased from Selleckchem (TX, USA). Sulforhodamine B (SRB) and other chemicals were obtained from Fisher Scientific or Sigma Chemical Company (St. Louis, Mo.).

Cancer Cell Lines:

Six human cancer cell lines have been used to evaluate effects of the compounds on proliferation of cancer cells. These cell lines include HCC827-P (or HCC827 parent cells), human non-small lung cancer cells, Parent NSCLC HCC827 cell line (which harbors EGFR gene amplification, Exon 19 (E19) deletion, and Exon 21 mutation (Wang, Ramakrishnan et al. 2010), and is an EGFRi sensitive cell line (Kim, Kim et al. 2010)); HCC827-TR16 (Tarceva-resistant HCC727 cell line), HCC827-OR16 (AZD9291-resistant HCC727 cell line), LNCaP (human prostate cancer cells—a hormonal-therapy sensitive cell line (Wang, Liu et al. 1997)); 22RV1 (human prostate cancer cells—a hormonal-therapy resistant cell line (Sramkoski, Pretlow et al. 1999)); and ACHN (human renal adenocarcinoma cells (Park, Jung et al. 2003)). LNCaP cells and 22RV1 cells were purchased from the American Type Culture Collection (Rockville, Md.) and others were gifts of friends.

To evaluate activities of new compounds on growth of EGFR-inhibitor-resistant cells, two EGFRi-resistant cell lines, i.e., HCC827-TR16 and HCC827-0R16 were established using a method described by Eberlein et al. (Eberlein, Stetson et al. 2015). HCC827—P cells grown exponentially were exposed to 0.5 µM of Tarceva or AZD9291 for a week (cycle 1). The cells were then reseed in fresh 10% FBS RPMI1640 medium, and retreated with 0.5 µM of Tarceva or AZD9291 for another week (cycle 2), and so on. Resistant cells were collected and stabilized after 5 weeks (cycle 5). The resistant cells were continuously exposure to 0.5 µM either Tarceva or AZD9291 until week $16^{th}$ (cycle 16). The resistant cells were sorted using 96-well dishes by culturing cells with density of 0.1, 1, 10, and 100 cells per well. Single colony was picked-up and HCC827-TR16 (resistance to Tarceva) and HCC827-0R16 (resistance to AZD9291) were obtained. The cells were then maintained and cultured in 10% FBS RPMI1640 medium without addition of Tarceva or AZD9291.

Results and Discussion:

Human epidermal growth factor receptors (EGFRs) have drawn much attention as attractive targets of anticancer drugs owing to their aberrant activities in many epithelial tumors. We therefore have designed several classes of molecules targeting EGFR, tested anti-proliferative activities using different types of human cancer cell lines, and calculated $IC_{50}$ as shown in Table 1 for each compounds in order to compare their strength of anti-proliferative effects.

To increase solubility and to mimic endogenous ligand structure of EGFR, we made a series of compounds that contain a sugar group or their intermediates and tested their activities. It appears that these compounds (compound Reno-308-1 to Reno-308-4) were less effective in almost all tested cancer cell lines ($IC_{50}$>10 µM). We believe that the position of sugar molecule as well as the type of sugar molecules may play a critical role in determining the activities of corresponding compounds.

TABLE 1

$IC_{50}$ of Tested Compounds in Various Human Cancer Cell Lines

| Compound | Formula | MW | $IC_{50}$ (µM) | | | | | |
| --- | --- | --- | --- | --- | --- | --- | --- | --- |
| | | | HCC827P | HCC827OR16 | HCC827TR16 | LNCaP | 22RV1 | ACHN |
| Reno308-1 | $C_{14}H_{20}N_2O_5$ | 296 | >10 | >10 | N/A | >10 | >10 | N/A |
| Reno308-2 | $C_{16}H_{24}N_2O_5$ | 324 | >10 | >10 | N/A | >10 | >10 | N/A |
| Reno308-3 | $C_{14}H_{18}N_2O_5$ | 294 | >10 | >10 | N/A | >10 | >10 | N/A |
| Reno308-4 | $C_{24}H_{26}N_2O_{12}$ | 534 | >10 | >10 | N/A | >10 | >10 | N/A |
| Reno635 | $C_{19}H_{16}N_4O_4$ | 364.35 | >5.0 | >5.0 | N/A | N/A | 5.0 | 3.75 |
| Reno636 | $C_{26}H_{20}BrN_5O_5$ | 562.37 | 0.20 | >5.0 | >5.0 | N/A | >5.0 | >5.0 |
| Reno645 | $C_{19}H_{18}N_4O_2$ | 334.37 | N/A | N/A | N/A | N/A | N/A | N/A |
| Reno647 | $C_{26}H_{20}FN_5O_5$ | 501.47 | 0.15 | 0.38 | 1.30 | 1.25 | 0.50 | 1.25 |
| Reno648 | $C_{26}H_{20}ClN_5O_5$ | 517.92 | 0.15 | >5.0 | >5.0 | >5.0 | >5.0 | N/A |
| Reno649 | $C_{26}H_{20}IN_5O_5$ | 609.37 | 0.20 | 1.8 | >5.0 | >5.0 | 2.3 | N/A |
| Tarceva | | | <0.2 | >5.0 | >5.0 | >5.0 | >5.0 | 0.625 |
| AZD9291 | | | <0.2 | 2.0 | 1.2 | 2.0 | 0.65 | N/A |

All cell lines were maintained in RPMI-1640 (GIBCO, Gaithersburg, Md.) with 10% heat-inactivated bovine serum (FBS) (Wang, Ossowski et al. 2004).

Evaluation of Cell Proliferation by SRB Method:

Sulforhodamine B (SRB) was used to estimate cell growth as described previously (Skehan, Storeng et al. 1990). Briefly, cells grown exponentially were aliquoted into 96-well plates at a density of 2,500 to 5,000 cells/200 µl per well in RPMI 1640 medium containing 10% FBS. After twenty-four hours, the cells were exposed to indicated concentrations of tested compounds for 72 hrs or otherwise as indicated. The cells were then fixed with 10% trichloride acetic acid for 2 h at 4° C. The 10% trichloride acetic acid was removed, and the dishes were washed 5 times with tape water, and air-dried. The fixed and dried cells were then stained with 0.4% SRB in 1% acetic acid for 25 min, and the dishes were washed 5 times with 1% acetic acid and air-dried overnight. 200 µl of 10 mM of Tris buffer (pH 10.0) were added, and the dishes were rotated to completely dissolve the color. Absorbance at 570 nm, with a reference wavelength 690 nm, was measured on a 96-well microplate reader (SPECTRO Star$^{Nano}$, BMG Labtech). Mean, standard deviation (SD) and the percent of growth inhibition at each concentration point of the treatment were calculated. The percent of growth inhibition as defined as $(1-T/C) \times 100$ where T is the mean of the absorbance at 570 nm from the treatment, and C from control (drug vehicle only). $IC_{50}$ was calculated using Sigma-plot software by regression of growth-concentration curve from each drug treatment.

Figure 2:
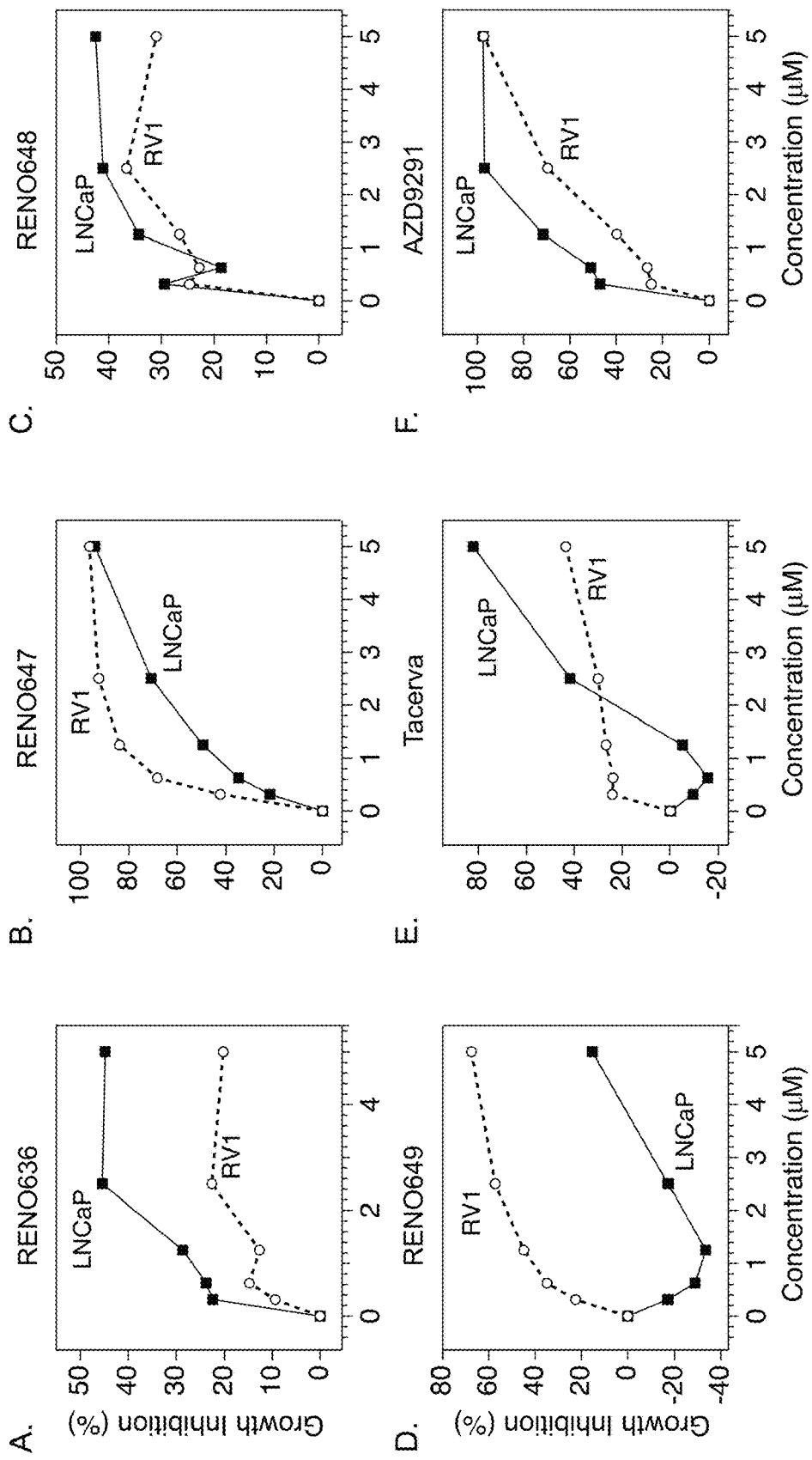
FIG. 2 depicts the effects of example Renotinibs (panels A-D), Tarceva (panel E), and AZD9291 (panel F) on growth inhibition against androgen-dependent LNCaP and androgen-independent 22RV1 prostate cancer cells. Cells grown exponentially were aliquoted into 96-wells plates at a density of 3,000 cells/200 µl per well in RPMI 1640 medium containing 10% FBS. After 24 hrs of incubation, cells were exposed to the indicated concentrations of tested compounds for 72 hrs. Cell growth was then measured by SRB method as described in the section of Example 2.1. Mean, standard deviation (SD) and the percent of growth inhibition at each concentration point of the treatment were calculated. Percent of growth inhibition is defined as (1-T/C)×100, where T is the mean of the absorbance at 570 nm from the treatment and C from control (drug vehicle only).

In FIG. 1, panels B and C provide typical concentration-effect curves of tested positive control compounds Tarceva and AZD9291 against HCC827-P and its AZD9291 resistant HCC827-0R16. While the parent HCC827 P cells were very sensitive to both Tarceva and AZD9291 treatment with an $IC_{50}$ around less than 0.2 µM, the resistant cell line HCC827-OR16 were clearly resistant to both of them, in particular to Tarceva where $IC_{50}$ was almost unmeasurable. In contrast, either HCC827P or HCC827-OR16 cells were sensitive to Reno647 treatment with similar $IC_{50}$ ($IC_{50}$ are 0.15 and 0.38 µM, respectively, FIG. 1 panel A). In addition, the tested both hormonal sensitive and refractory prostate cancer cell lines LNCaP and 22RV1 cells were also sensitive to Reno647, in particular, the hormonal refractory 22RV1 cells with $IC_{50}$ around 0.5 µM (Table 1 and FIG. 2). But both cell lines showed relatively weak response to Tarceva treatment indicating that Tarceva cannot be used to treat prostate cancer. Overall, Reno636, Reno647, Reno648, and Reno649 showed better activities against all tested cancer cells lines than that of NK-2206, a Akt (downstream of EGFR) inhibitor, and MLN8237, a newly developed AURORA-A inhibitor currently in clinical trials for various human cancer including refractory prostate cancer (data not provided).

2.2 Inhibition of Combination of Reno 647 with Chemotherapeutical Agents on Cancer Cell Growth Reno647:

Reno647 tested in this section was synthesized as described in Example 1, structurally characterized by NM, MS, and purified by HPLC with a purity >98.0%.

Reagents:

Tarceva was purchased from Selleckchem (TX, USA). Paclitaxel, Carboplatin, sulforhodamine B (SRB) and other chemicals were obtained from Fisher Scientific, Santa Cruz Biotechnology or Sigma Chemical Company (St. Louis, Mo.).

Cancer Cell Lines:

As described in Example 2.1. Two cell lines, HCC827-P and HCC827-TR (Tarceva-resistant HCC727 cells,—an EGFRi resistant cell line with MET amplification)(Wang, Pursell et al. 2013) were used in the combination study.

Combination Analysis:

Exponentially growing HCC827P and HCC827-TR cells were seeded into 96-wells dishes at density of 3,000 cells per well. Twenty-four hours later, the cells were exposed concurrently to serial dilution of Reno647 or Carboplatin or Camptothecin alone or in combination at a ratio of 1:50 with Carboplatin or at ratio 1:1 with Camptothecin for 3 days. Reno647 were concurrently and sequentially with paclitaxel (Taxol) at ratio of 200:1 for 6 days. For sequential exposure, the cells were treated with Reno647 for 3 days, after removal of the drug containing medium, the cells were treated with Taxol for additional 3 days, or the cells were treated by Taxol first followed by the treatment with Reno 647. After incubation for 6 days, the cell growth was measured by SRB as described previously in Example 2.1 section, and the percentages of inhibition (1−T/C) % were calculated, and data were analyzed by a PC program, CalcuSyn, Biosoft (edited by T.-C. Chou, Memorial Sloan-Kettering Cancer Center, New York, and M. P. Hayball, at Cambridge, UK, 1996). The computer-calculated combination index (CI) was used to judge the outcomes of a combination: CI>1, CI=1, and CI<1 indicating antagonistic, additive, and synergistic effects, respectively (Chou, Motzer et al. 1994).

Results and Discussion:

Earlier studies showed that combination of EGFRi with standard conventional chemotherapeutic agents against lung cancer, neither platinum drugs nor taxanes achieved overall survival (OS) benefits (Herbst, Prager et al. 2005; Gatzemeier, Pluzanska et al. 2007). Since Reno647 contains structural characteristics of both EGFRi and PARPi functional groups, we expect combinations of Reno 647 with platinum compounds or taxanes or Camptothecin will achieve synergistic or at least additive therapeutic effects.

2.2.1 Concurrent Combination of Reno 647 with Carboplatin is Synergistic in Growth Inhibition in Both HCC827 P and HCC827 TR It has long been accepted that chemotherapy provided some benefit for patients with non-small-cell lung cancer (NSCLC) in terms of quality of life and symptomatology as well as modest improvements in survival. Carboplatin (Paraplatin), the less-toxic analogue of cisplatin, has been shown to produce a superior 1-year survival rate of 28% with considerably less toxicity than was seen with the cisplatin-based combination regimens (http://www.cancernetwork.com/review-article/paclitaxelcarboplatin-treatment-non-small-cell-lung-cancer). To explore if the combination of Reno647 and Carboplatin produces desired therapeutic effects (synergistic or at least additive effects) on inhibition of non-small lung cancer cell growth, both parent HCC827 P and Tarceva refractory HCC827 TR cells were exposed to Reno647 or carboplatin alone or two drug in combination concurrently at a ratio of 1:50 (Reno647: carboplatin) for 6 days. Cell growth was determined by SRB as described above.

Figure 3:
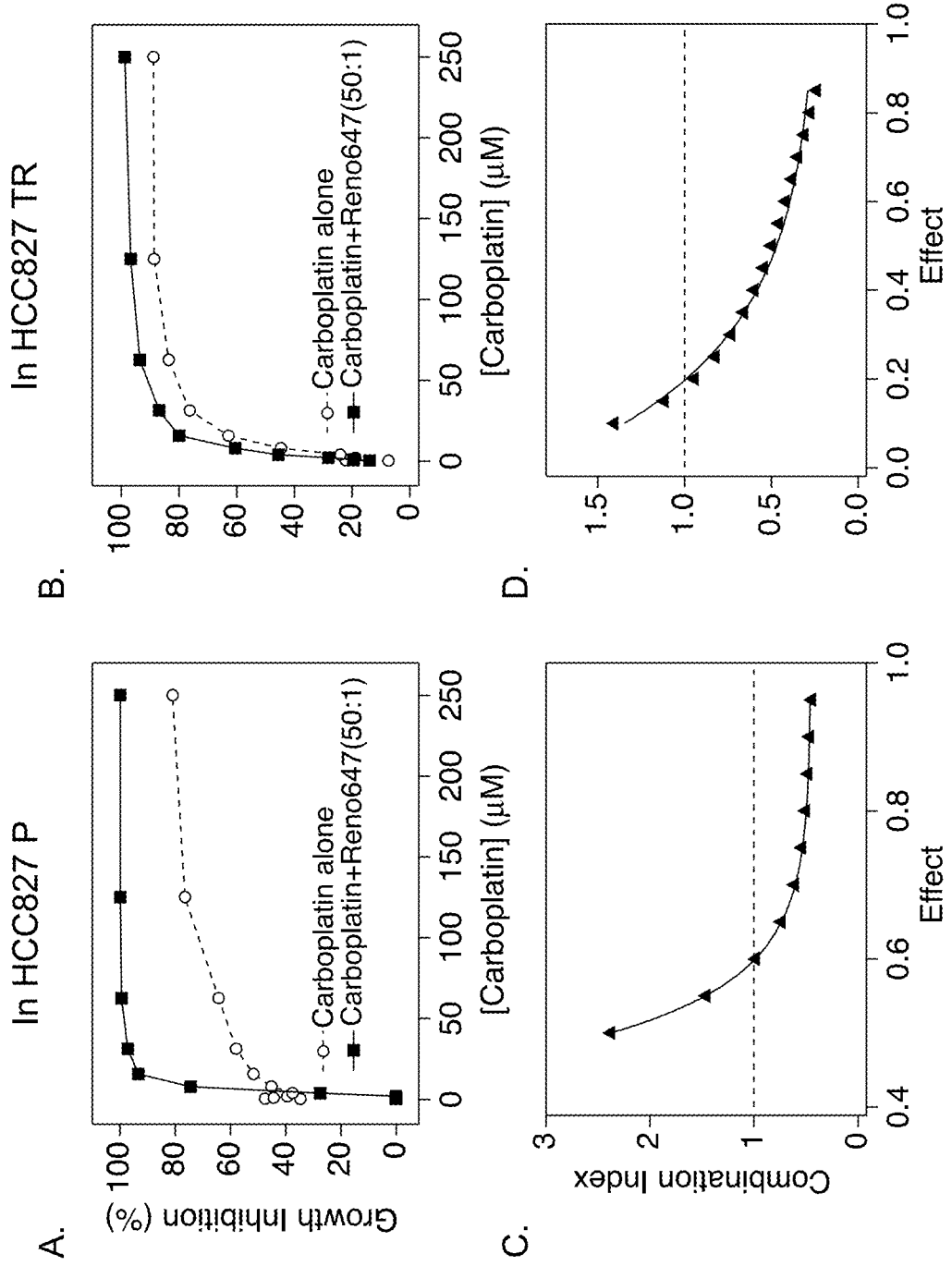
FIG. 3 depicts analysis of outcomes of cell growth inhibition of the combination of Reno647 and Carboplatin in parent HCC827 P (panels A and C) and in HCC827 TR cells (panels B and D). HCC827 P and in HCC827 TR cells at exponential growth phase in 96-wells dishes were exposed to series concentrations of either Reno647 or Carboplatin or both at ratio of Reno647 over Carboplatin 1:50 for 6 days. Cell growth under various drug treatment conditions was measured by SRB method using a 96-wells dish reader at 570/690 nm. Growth inhibition rate was calculated as follows: growth inhibition rate=1−T/C, where T is the value of drug-treated cells and C is the value of vehicle-treated cells. The combination index (CI) was calculated by computer program CalcuSyn. IC equaling one (blue dish line, panels C&D) indicates an additive effect; IC being more than one indicates an antagonistic effect; and IC being less than one indicates a synergistic effect. The pink line indicates the trend of the combination index.
Figure 4:
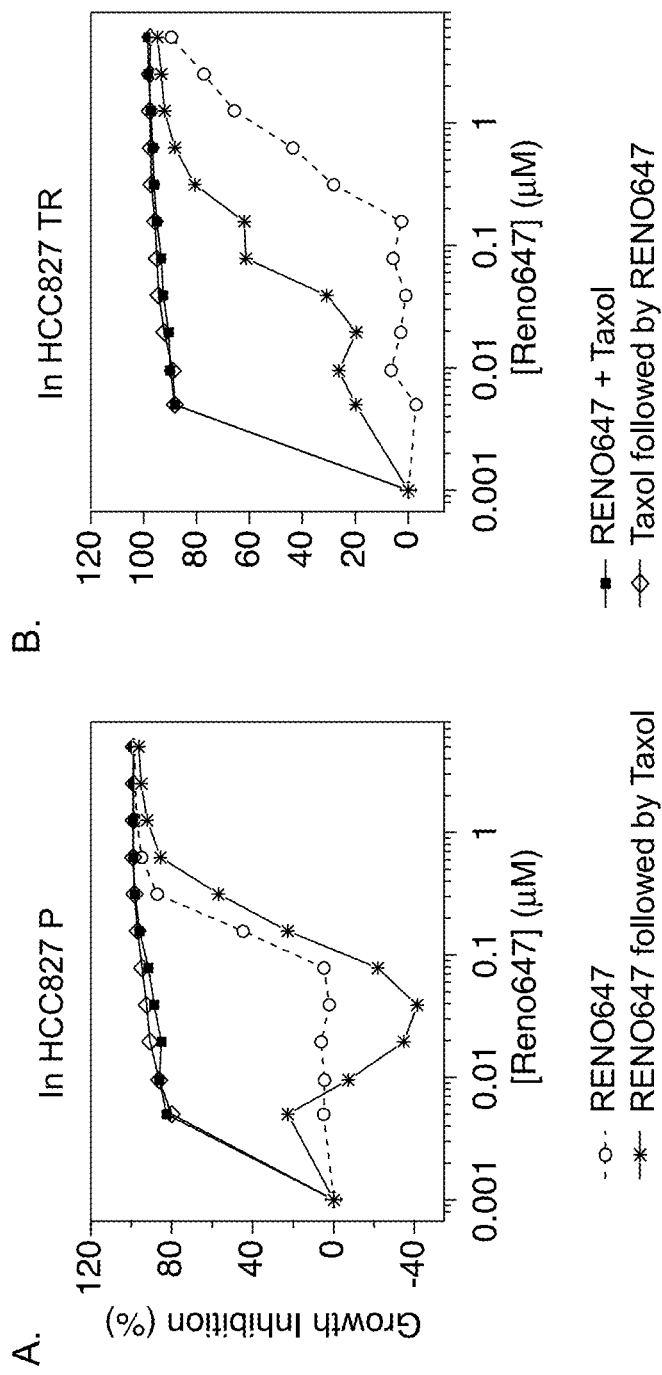
FIG. 4. Analysis of outcomes of cell growth inhibition of Reno 647—Camptothecin combination in parent HCC827 P and in HCC827 TR cells. HCC827 P and in HCC827 TR cells at exponential growth phase in 96-wells dishes were exposed to series concentrations of either Reno647 or Camptothecin or both at ratio of Reno647 over Camptothecin 1:1 for 3 days. The cell growth under various drug treatment conditions was measured by SRB method using a 96-wells dish reader at 570/690 nm. The growth inhibition rate was calculated using equation 1−T/C, where T is the value of treated cells, and C is the value of vehicle-treated cells. The combination index (CI) was calculated by computer program CalcuSyn. IC equal one (blue dish line, panel C&D) indicates an additive effect, more than one is antagonistic effect and less than one is synergistic effect. Pink line indicates the trend of the combination index.

FIG. 3 shows the results of the Reno647/Carboplatin combination. Significant synergistic effects were observed in both parent HCC827 P and the Tarceva refractory HCC827 TR cells (FIG. 3 panels C and D, CIs were well below 1 at effective concentrations). It is noted that the dose reduction was significant, particularly that for Reno647 with a 10-fold decrease. For example, the median effects of Reno647 and Carboplatin alone were 0.697 and 8.39 μM, respectively. When the two drugs were combined, the median effects were reduced to 0.067 and 3.38 μM, respectively. This finding suggests that the same efficacy can be achieved clinically at over a 10-fold decrease of Reno647 and a 2-fold decrease of Carboplatin when they are combined. In addition, treatment of the cells with Carboplatin alone, the growth inhibition was not found to be able to reach 100%, this however was easily achieved with two drug combination (FIG. 4, A & B).

2.2.2 Concurrent Combination of Reno647 with Camptothecin is Synergistic in HCC827 P and HCC827 TR Camptothecin is a DNA topoisomerase inhibitor that produces extensive (single strand breaks (SSBs)). Since in Reno647, an PARP inhibitor was fused into the molecule, we expect Reno647 also inhibits PARP1/2 to some extent. If so, it should be able to enhance activity of an DNA damage agent. To explore if the combination of Reno647 and Camptothecin produces desired therapeutic effects (synergistic or at least additive effects) on inhibition of non-small lung cancer cell growth, both parent HCC827 P and Tacerva refractory HCC827 TR cells were exposed to Reno647 or camptothecin alone or two drugs in combination concurrently at ratio of 1:1 (Reno647: carbolatin) for 3 days. Cell growth was determined by SRB as described above. As expected, significant synergistic effects were observed in both parent HCC827 P and the Tacerva refractory HCC827 TR cells when Reno647 was combined with Camptothecin as ratio 1:1. (FIG. 4 C&D, CIs were well below 1 at effective concentration), particularly at higher concentration where Reno647 achieves its effective inhibition on PARP. This data further indicates that Reno647 also inhibits PARP activity.

2.2.3 Synergistic Effects Between Reno647 and Paclitaxel are Sequence Dependent in Both HCC827 P and HCC827 TR It has been reported that paclitaxel (Taxol) transiently induced EGFR phosphorylation and ERK and AKT activation, which was suggested that combination of EGFR inhibitors with Taxol might enhance Taxol's activity (Qiu, Di et al. 2005). However, induction of EGFR activation mediated by Taxol may compromise activity of EGFR inhibitors. To examine our hypothesis, Taxol was combined with Reno647 in three different sequential exposures:

Combination 1: exposure of HCC827P or TR cells to Reno647+Taxol simultaneously for 6 days.

Combination 2: exposure of the cells to Reno647 first for 3 days followed by treatment with Taxol for an additional 3 days, or Combination 3: exposure of the cells to Taxol first for 3 days followed by treatment with Reno647 for an additional 3 days.

Exposure of the cells to either Reno647 or Taxol served as controls. After exposure, cell growth was determined by SRB and analyzed as described in above section.

Figure 5:
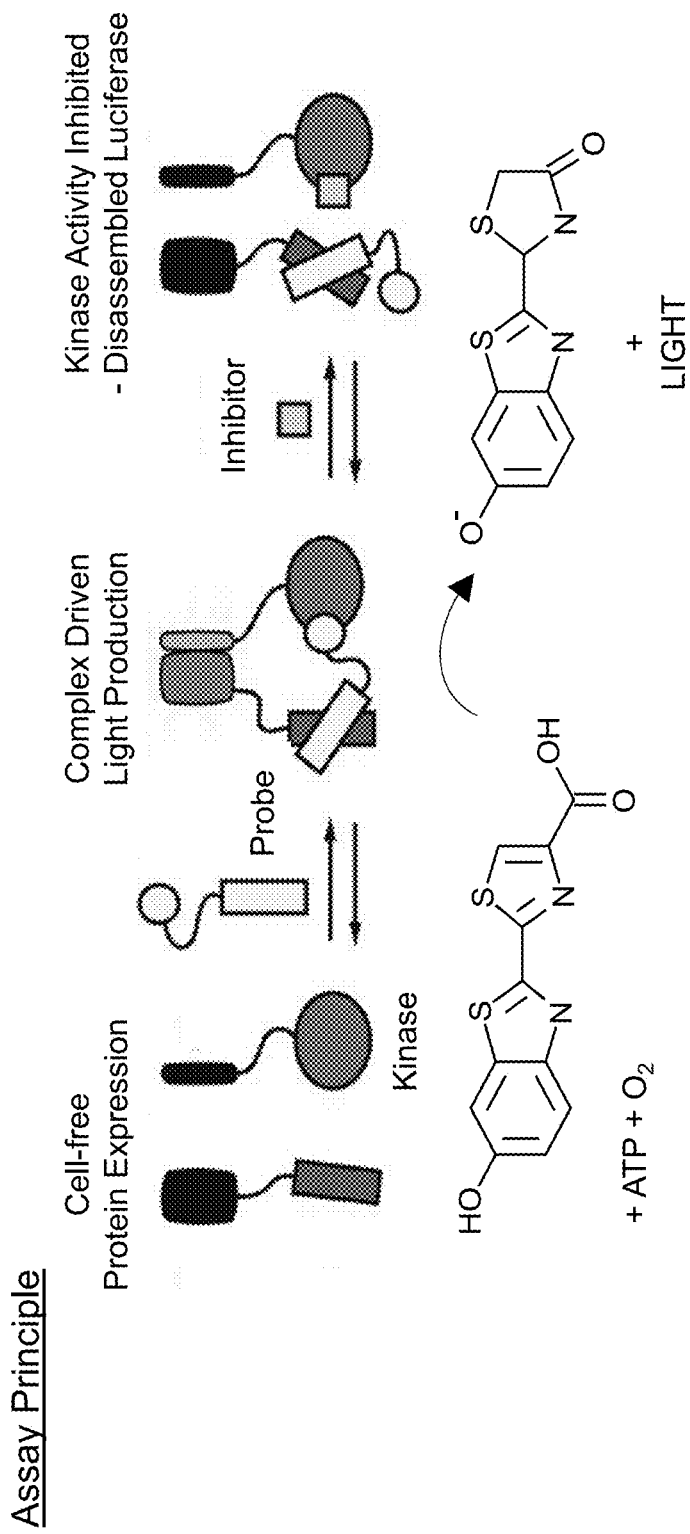
FIG. 5 depicts the effects on cell growth of HCC827 P (panel A) and HCC838 TR (panel B) with different treatment regimens involving a combination of Reno647 and Taxol: exposure to Reno747 and Taxol concurrently for 6 days; exposure to Taxol for 3 days followed by Reno647 for 3 days; and exposure to Reno647 for 3 days followed by Taxol for 3 days. Exposure to either Reno647 or Taxol for 6 days serves as the baseline for analysis of combination outcomes. Cell growth under various drug treatment conditions was measured by SRB method using a 96-wells dish reader at 570/690 nm. Growth inhibition rate was calculated as follows: growth inhibition rate=1−T/C, where T is the value of drug-treated cells and C is the value of vehicle-treated cells. The combination index (CI) was calculated by computer program CalcuSyn. IC equaling one (blue dish line, panels C&D) indicates an additive effect; IC being more than one indicates an antagonistic effect; and IC being less than one indicates a synergistic effect. The pink line indicates the trend of the combination index.
Figure 6:
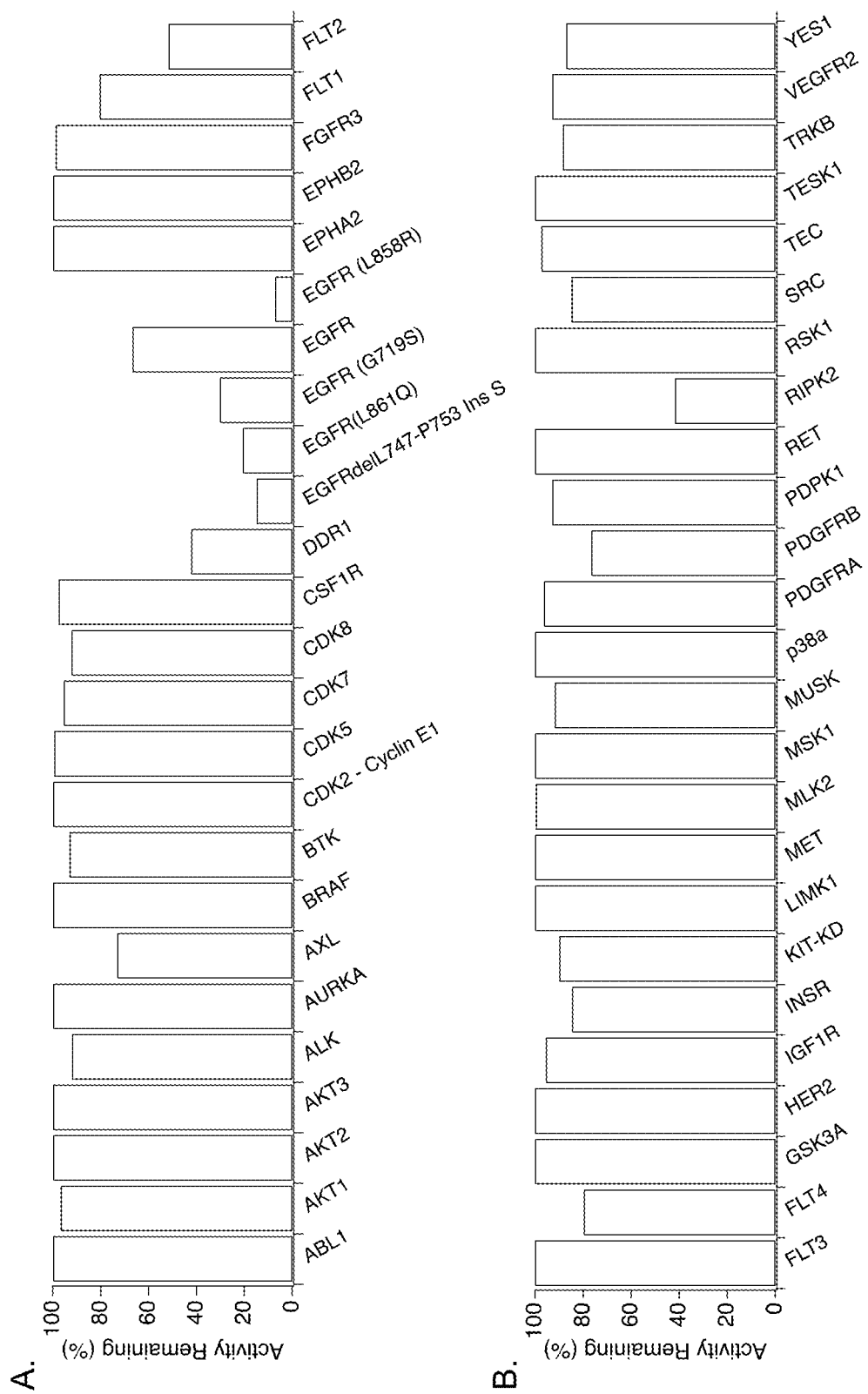
FIG. 6 depicts the principle of the kinase assay of Example 3.

As shown in FIG. 5, outcomes of the combination of Reno647 with the anti-microtubule agent Taxol were found to be highly dependent on sequence of the drug exposure. A strong synergistic cell growth inhibition (CI<1) in both HCC827P and HCC827TR non-small lung cancer cell lines was achieved when the cancer cells were concurrently exposed to Reno647 and Taxol or to Taxol first followed by Reno647. However, a strong antagonistic effect (CI>1) was observed when the cells were exposed to Reno647 first followed by Taxol, which may be resulted from a reactivation of EGFR by Taxol. These findings suggest that concurrently combined Reno647 with Taxol or treatment with Taxol followed by Reno647 at a ratio of 200 to 1 will most likely achieve significant synergistic effects against both naive EGFRi sensitive or Tarceva refractory non-small lung cancer. Addition of Reno647 to patients under Taxol chemotherapy may also produce beneficial effects. However, a reverse combination, where Reno647 is given followed by Taxol, should be avoid as it may produce a strong antagonistic outcome.

3. Effect on Kinase Activation 3.1. Kinase Profiling:

Kinase Panel:

Compound Reno647 was profiled against the following panel of kinases at 2 μM using the KinaseSeeker™ assay: ABL1, AKT1, AKT2, AKT3, ALK, AURKA, AXL, BRAF, BTK, CDK2, CDK5, CDK7, CDK8, CSF1R, DDR1, EGFR del L747-P753 InsS, EGFR (L861Q), EGFR (G719S), EGFR, EGFR (L858R), EPHA2, EPHB2, FGFR3, FLT1/VEGFR1, FLT2/FGFR1, FLT3, FLT4/VEGFR3, GSK-3a, HER2, IGF1R, INSR, KIT, LIMK1, MET, MLK2/MAP3K10, RPS6KA5/MSK1, MUSK, p38a/MAPK12, PDGFRA, PDGFRB, PDK1, RET, RIPK2, RPS6KAI/RSK1, SRC, TEC, TESK1, TRKB, VEGFR2, and YES1.

Assay Design:

KinaseSeeker is a homogeneous competition binding assay where the displacement of an active site dependent probe by an inhibitor is measured by a change in luminescence signal (see FIG. 5). Luminescence readout translates into a highly sensitive and robust assay with low background and minimal interference from test compounds.

Assay Method (Jester, Cox et al. 2010; Jester, Gaj et al. 2012): 10 mM stock of compound Reno647 was diluted in DMSO to a concentration of 50 μM. Prior to initiating a profiling campaign, the compound was evaluated for false positive against split-luciferase. The compound was then screened in duplicate against each of the kinases. For kinase assays, each Cfluc-Kinase was translated along with Fos-Nfluc using a cell-free system (rabbit reticulocyte lysate) at 30° C. for 90 min. A 24 μL aliquot of this lysate containing either 1 μL of DMSO (for no-inhibitor control) or compound solution in DMSO (2 μM final concentration) was incubated for 30 minutes at room temperature followed by 1 hour in the presence of a kinase specific probe. A 80 μL of luciferin assay reagent was added to each solution and luminescence was immediately measured on a luminometer.

The % Inhibition and % Activity Remaining were calculated using the following equations:

$$\% \text{ inhibition} = \frac{(ALU_{control} - ALU_{sample})}{ALU_{control}} \times 100$$

% activity=100−% inhibition.

Profiling data for all kinases was plotted as % activity remaining vs. kinases profiled. A heat map representing the effect of compound on kinases was also generated.

Results and Discussion:

In order to examine whether core structure (Formula I) compounds in this invention are able to target EGFR as designed, we applied Reno647 as example compound for kinase profiling against 50 kinases (see section of Kinase Panel) using KinaseSeeker. As shown in Table 2, Reno647 significantly and selectively inhibited EGFR at concentration 2 μM, in particular mutated forms of EGFR (EGFR del L747-P753 Ins S (14.8% remaining activity), EGFR (L861Q, 20.7% remaining activity), EGFR (G719S, 30.2% remaining activity), and EGFR (L858R, 7.2% remaining activity)), but much less extent to wild-type EGFR (66.7% remaining activity under the same experimental conditions). It also showed mild inhibitory activity against DDR1 (approximately 42% remaining activity) and RIPK2 (approximately 41% remaining activity). The specificity was reflected by the fact that there were no significant inhibitory activities against all other kinases in the tested panel (over 50% remaining activity). These data demonstrate that the core structure compounds are selective inhibitors against mutated EGFR.

TABLE 2

KinaseSeeker ™ Profile for Reno647 at 2 μM Concentration % Activity Remaining

| Kinase | Family | 0%         50%         100%<br>% Activity Remaining<br>Reno647 (2 uM) | HEAT MAP<br>Reno647 (2 uM) |
|---|---|---|---|
| Set 1 | | | |
| ABL1 | TK | 100.0 | |
| AKT1 | AGC | 96.8 | |
| AKT2 | AGC | 100.0 | |
| AKT3 | AGC | 100.0 | |
| ALK | TK | 92.1 | |
| AURKA | Other | 100.0 | |
| AXL | TK | 73.2 | |
| BRAF | TKL | 100.0 | |
| BTK | TK | 93.1 | |
| CDK2-Cyclin E1 | CMGC | 100.0 | |
| CDK5 | CMGC | 99.5 | |
| CDK7 | CMGC | 95.5 | |
| CDK8 | CMGC | 92.3 | |
| CSF1R | TK | 97.6 | |
| DDR1 | TK | 42.3 | |
| EGFR del L747-P753 Ins S | TK | 14.8 | |
| EGFR (L861Q) | TK | 20.7 | |
| EGFR (G719S) | TK | 30.2 | |
| EGFR | TK | 66.7 | |
| EGFR (L858R) | TK | 7.2 | |
| EPHA2 | TK | 100.0 | |
| EPHB2 | TK | 100.0 | |
| FGFR3 | TK | 98.9 | |
| FLT1 | TK | 80.5 | |
| FLT2 | TK | 51.7 | |
| Set 2 | | | |
| FLT3 | TK | 100.0 | |
| FLT4 | TK | 79.8 | |
| GSK3A | CMGC | 100.0 | |
| HER2 | TK | 100.0 | |
| IGF1R | TK | 95.5 | |
| INSR | TK | 84.6 | |
| KIT-KD | TK | 90.0 | |
| LIMK1 | TKL | 100.0 | |
| MET | TK | 100.0 | |
| MLK2 | TKL | 99.7 | |
| MSK1 | AGC | 100.0 | |
| MUSK | TK | 91.8 | |
| p38a | CMGC | 100.0 | |
| PDGFRA | TK | 96.4 | |
| PDGFRB | TK | 76.6 | |
| PDPK1 | AGC | 92.8 | |
| RET | TK | 100.0 | |
| RIPK2 | TKL | 41.8 | |
| RSK1 | AGC | 100.0 | |

TABLE 2-continued

KinaseSeeker ™ Profile for Reno647 at 2 µM Concentration
% Activity Remaining

| Kinase | Family | % Activity Remaining Reno647 (2 uM) | HEAT MAP Reno647 (2 uM) 0% 50% 100% |
|---|---|---|---|
| SRC | TK | 84.9 | |
| TEC | TK | 97.4 | |
| TESK1 | TKL | 100.0 | |
| TRKB | TK | 88.4 | |
| VEGFR2 | TK | 92.8 | |
| YES1 | TK | 87.1 | |

3.2. Determination of IC$_{50}$ on Inhibition of EGFR:

Assay Design:

The same assay design was used as described in example section 3.1.

Assay Method:

10 mM stock solutions of compound Reno647 was serially diluted in DMSO to make assay stocks. Prior to initiating IC50 determination, the test compound was evaluated for false positive against split-luciferase.

Reno647 was screened against 6 kinases (EGFR, EGFR del L747 P753 InsS, EGFR G719S, EGFR L858R, EGFR L861Q, RIPK2) at a minimum of 8 different concentrations in duplicate. For kinase assays, a 24 µL aliquot of lysate containing Cfluc-kinase and Fos-Nfluc was incubated for 30 minutes at room temperature with either 1 µL of DMSO (for no-inhibitor control) or compound solution in DMSO, followed by 1 hour incubation in the presence of a kinase specific probe. A 80 µL of luciferin assay reagent was added to each solution and luminescence was immediately measured on a luminometer.

The % Inhibition and % Activity Remaining was calculated using the following equations:

$$\% \text{ inhibition} = \frac{(ALU_{control} - ALU_{sample})}{ALU_{control}} \times 100$$

% activity = 100 − % inhibition.

The % Activity was plotted against compound concentration and the IC50 was determined for each compound using an 8-point curve.

Figure 7:
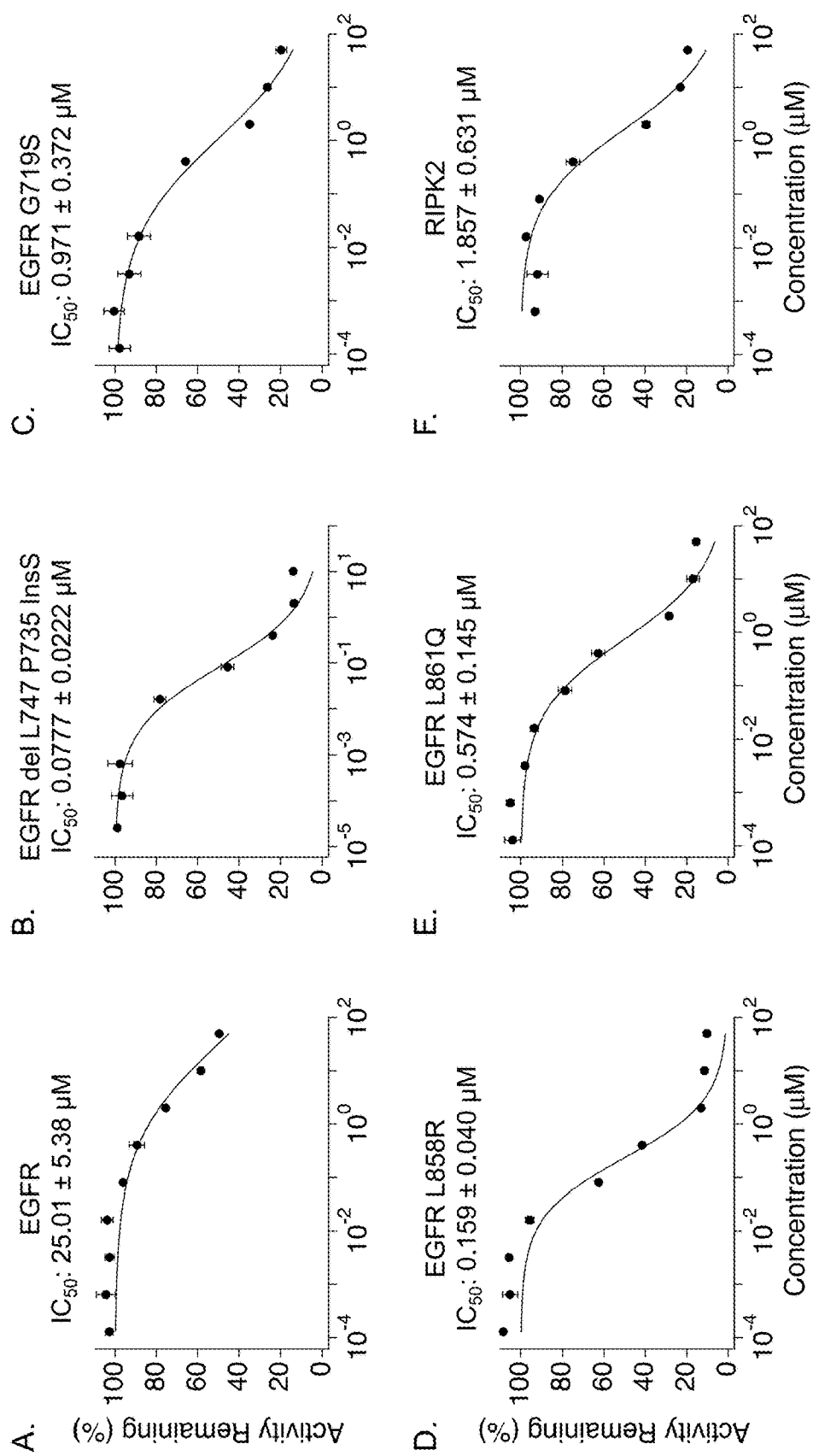
FIG. 7 depicts the effects of Reno647 against 6 kinases (EGFR, EGFR del L747 P753 InsS, EGFR G719S, EGFR L858R, EGFR L861Q, and RIPK2) at a minimum of 8 different concentrations in duplicate. For kinase assays, a 24 µL aliquot of lysate containing Cfluc-kinase and Fos-Nfluc was incubated for 30 minutes at room temperature with either 1 µL of DMSO (for no-inhibitor control) or compound solution in DMSO, followed by 1 hour incubation in the presence of a kinase specific probe. Luciferin assay reagent (80 µL) was added to each solution and luminescence was immediately measured on a luminometer.

Results and Discussion:

To further examine activity of the core compounds in this invention against mutated EGFR, we determined IC50 of Reno647 on various forms of EGFR using KinaseSeeker as described in example section 3.1. As expected, Reno647 strongly and selectively inhibited mutated EGFR (FIG. 7), the IC50 for the mutated EGFR del L747-P753 InsS, EGFR (G719S), EGFR (L858R), and EGFR L861Q was found to be 0.0777, 0.971, 0.159, and 0.574 µM, respectively. Again, the inhibition of Reno647 on the wild-type of EGFR was very weak, reflected by its IC50 25.01 µM.

Dysregulation of EGFR has been demonstrated in various types of human cancer, such as head and neck, breast, bladder, ovarian, renal, colon, non-small lung cancer, etc. (Yewale, Baradia et al. 2013) and excessively expressed and activated in cancer cells as the result of various mutations, amplifications, and ligand-dependent and independent activation. Thus, EGFR has become an attractive target for anti-cancer drugs. More importantly, among various type of mutations EGFR exon 19 del and EGFR L858R are two major mutated forms occurred clinically, and account for 48.2% and 42.7% of EGFR mutations, respectively (Mitsudomi, Kosaka et al. 2006; Rosell, Moran et al. 2009). Important to note that these two major forms of mutations were knocked down the most by Reno647 with inhibitory IC50 0.077 and 0.159 µM, and there was almost no effect on the wild-type of EGFR (25.01 µM as compared with 0.077 µM on EGFR exon 19 del). These observations, which parallel very well with cell growth inhibition described in the Example 1, further demonstrate that the core compounds described in this invention are expected to be novel drugs against various types of cancer without interfering with normal physiological functions of wild-type EGFR.

4. Effects of Renotinibs on Downstream Signals of EGFR Pathway

Materials and Methods

Reagents:

Primary antibodies against pEGFRTyr1068; pEGFRTry845; pAktSer473; MEK1/2; pMEK1/2; p27; and pp70-S6 kinase 2 were purchased from Cell signaling Technology. β-actin, for loading control, was purchased from Sigma Chemical Company (St. Louis, Mo.). Secondary antibodies were purchase from Santa Cruz Biotechnology (Dallas, Tex.). Reagents for protein SDS-PAGE and buffer as well as other materials/reagents for Western blot were purchased from BioRad (Hercules, Calif.). Kits for RNA extraction/purification, for cDNA preparation, for qRT-PCR analysis, as well as pre-designed primers and probe for qPCR, etc. were purchased from ThermoFisher Scientific (Waltham, Mass.), or otherwise as indicated.

Cell Treatment and Western Blotting:

HCC827 P or other indicated cells at exponential growth phase were treated with indicated compounds for 24 hrs. The cells were washed with PBS, harvested and cellular proteins were extracted. Twenty µg of proteins were subjected to 5%/7.5% or 5%/10% stacking SDS-PAGE, electro-transferred to Polyvinylidene difluoride (PVDF) membrane. Protein or phosphor-protein levels of pEGFRTyr1068; pEGFRTry845; pAktSer473; pp70 S6 kinase 2; MEK1/2; pMEK1/2; p27; and pp70 S6 kinase 2 were determined by Western blot as described previously using specific antibodies, respectively (Wang, Liu et al. 1997). β-actin was used as loading control.

RNA Isolation, cDNA Preparation and qRT-PCR:

HCC827 P or other indicated cells at exponential growth phase were treated with indicated concentrations of compounds for 24 hours. Total cellular RNA was prepared from lysed tumor cells using an RNA Purification kit (ThermoFisher Scientific). The first-strand of cDNA was synthesized using a High Capacity cDNA reverse transcription kit (ThermoFisher Scientific) in PTC-100 Peltier Thermal Cycler PCR. The resultant cDNA (0.5-1 µL) was used in a 10 ul reaction by using Taqman Universal PCR Master Mix (ThermoFisher Scientific). The pre-designed primers and probe were purchased from Life Technologies and used for qPCR. Human GAPDH was used as an internal control. qPCR was performed using Applied Biosystems StepOne and StepOnePlus Real-Time PCR Systems according manufacturer's instructions. An initial PCR denaturation step was performed at 95° C. for 20 seconds. The general cycling stage for qPCR were as follows: denaturation at 95° C. for 1 second, annealing and extension at 60° C. for 20 seconds, repeat for 40 cycles. Tgene ΔCt value was normalized for GAPDH by calculating ΔCt=Ctgene−CtGAPDH per sample.

Results and Discussion

Activation of EGFRs initiates downstream signaling cascades, including those involving Ras/Raf/mitogen-activated protein kinase (MAPK), PI3K/Akt/mTOR, and Jak/STATs, thereby trigging a variety of cellular response associated with the promotion of tumor growth, proliferation, survival, angiogenesis, invasion, and metastasis (Herbst and Shin 2002; Solomon, Hagekyriakou et al. 2003; Yu and Jove 2004; Hynes and Lane 2005; Takeuchi and Ito 2010). We expected that Renotinibs could affect those signal molecules. To examine this hypothesis, Western blots or qRT-PCR were used to determine activities or expression levels of those molecules.

Figure 8:
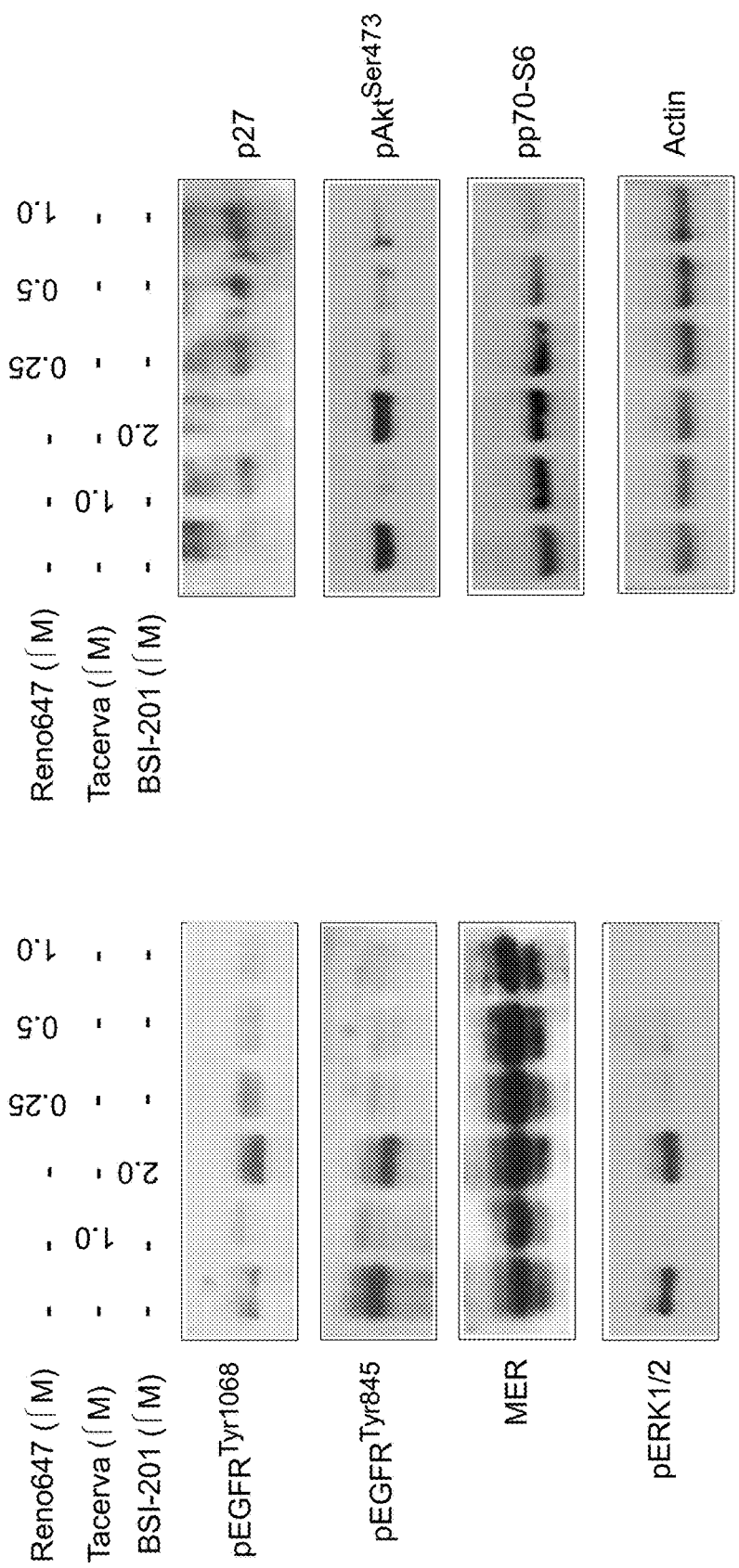
FIG. 8 depicts the effects of Reno647, Tarceva (positive control), or BSI-201 (negative control) on the activation of downstream signaling cascades of EGFR-related signaling. HCC827 P cells at exponential growth phase were treated with Reno647, Tarceva, or BSI-201 at the indicated concentrations for 24 hrs. The cells were washed with PBS, harvested and cellular proteins were extracted. Twenty µg of proteins were subjected to 5%/7.5% or 5%/10% stacking SDS-PAGE and electro-transferred to a PVDF membrane. Protein or phosphor-protein levels of pEGFRTyr1068, pEGFRTry845, pAktSer473, pStat3Tyr705, MEK1/2, pMEK1/2, p27, and pp70 S6 kinase 2 were determined by Western blot using specific antibodies. β-actin was used as loading control.

Downregulation of Ras/Raf/MEK Pathway:

FIG. 8 shows examples of Western blot. Similar to Tacerva, treatment of HCC827 P cells with Reno647, significantly decreased the levels of pEGFRTyr1068 and pEGFRTry845 in a concentration dependent manner. Parallel with these reductions, a significant decrease in the level of pERK1/2 (Ras/Raf/MEK pathway) was observed, whereas no changes were obtained on the total protein of MER. The inhibition on activation of Ras/Raf/MEK pathway was further supported by the induction of endogenous inhibitor of cyclin-dependent kinases, p27. A significant induction of endogenous inhibitor of cyclin-dependent kinases, p21, was also observed in both HCC827-P and AZD9291-resistant cell line HCC827-0R16 cells by q-RT-PCR shown in FIG. 9. The induction of p21 expression by Reno647 was found to be stronger than the positive control Tacerva, and AZD9291, which may be partly resulted from its inhibition on PARP since PARP inhibitors can induce p21 expression through interaction with the cell cycle checkpoint proteins of mutated Ataxia Telangiectasia (ATM) (Madison, Stauffer et al. 2011).

Examples of Renotinibs on PI3K/Akt/mTOR Pathway are also shown in FIG. 8. Phospho-Akt level was significantly reduced in a concentration dependent manner after the treatment of HCC827-P cells with Reno647. The suppression of Reno647 on the activation of Akt was further supported by the consequently significant decreases in pp-70-65 activity. p70-S6 is a serine/threonine kinase that acts downstream of PIP3 and phosphoinositide-dependent kinase-1 in the PI3 kinase pathway, and phosphorylation of S6 induces protein synthesis at the ribosome. Therefore, an inhibition of protein synthesis by Reno647 is expected as a result of its inhibition of p70-S6 activation. Interestingly, no such effect on p70-6S activation by Tacerva was observed under the same experimental conditions.

Figure 9:
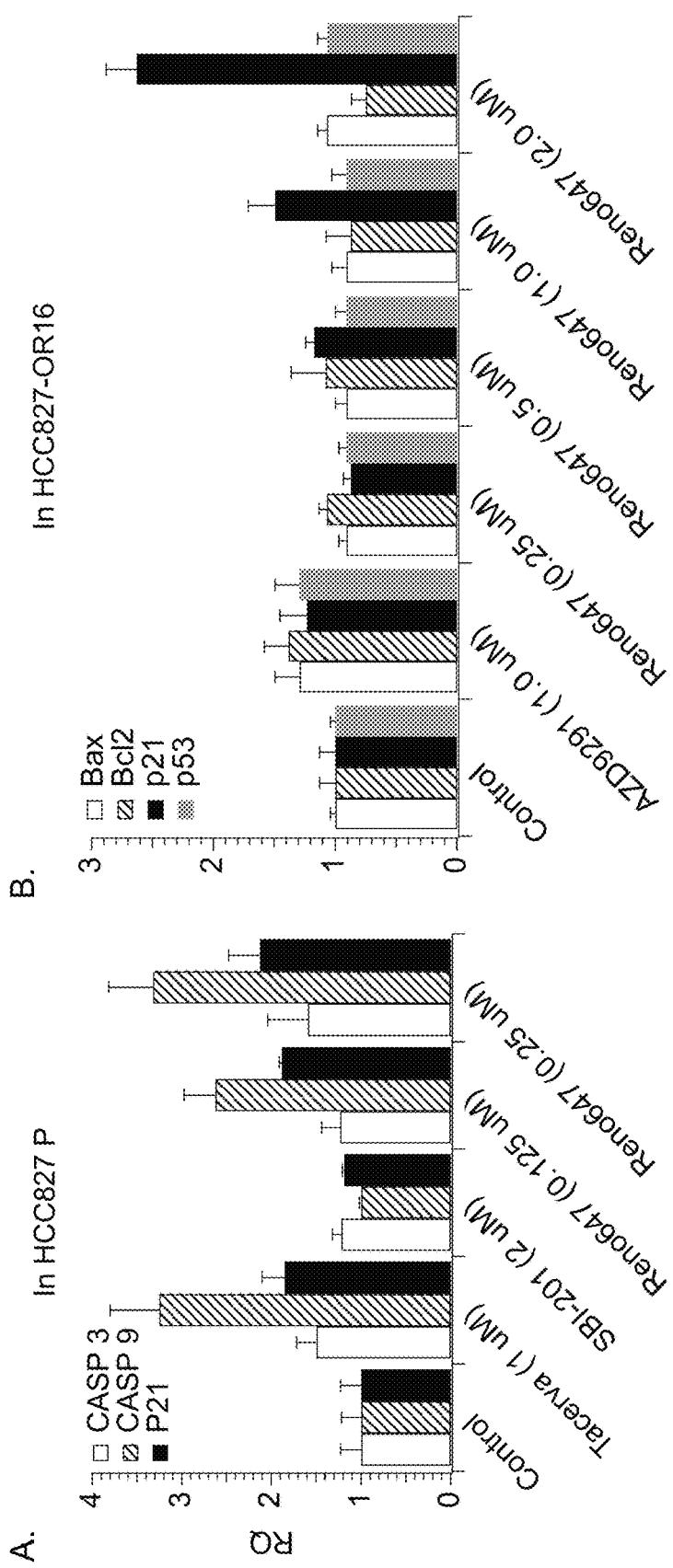
FIG. 9 depicts the effect of Reno647 on expressions of Caspase 3, Caspase 9 and p21 in HCC827-P and on Box, Bcl2, p53 and p21 in HCC827-0R16 cells. HCC827 P or OR16 cells at exponential growth phase were exposed to indicated concentration of Reno647, Tarceva, ADZ9291 (positive control, 2.0 µM) or 2.0 µM of BSI-201 for 24 h. Total cellular RNA was extracted and cDNA was prepared followed by qRT-PCR using specific probes as described in the section of Materials and Methods. Tgene ΔCt value was normalized for GAPDH by calculating ΔCt=Ctgene−Ct-GAPDH per sample.

Induction of Apoptosis and Inhibition on PD-L1 Expression:

EGFR mediated signal transduction also enhances cell survival ability through the Ras/MER, PI3K/Akt/mTOR as well as Jak/Stat3 pathways while assists tumor cells escaping from immune-attack by activation of death receptor ligands PD-LI and PD-L2 expression. To examine whether Renotinibs mediated inhibition on EGFR/PARP is able to trigger apoptosis process, the levels of expression of Caspase 3 and Caspase 9 were determined in HCC827-P and OR16 cells after the treatment with Reno647. An example is shown in FIG. 9, panel A where a significant and concentration-dependent induction of Caspase 9 expression was observed while expression of Caspase 3 showed a moderate increase. Similar result was also obtained in HCC827-OR16 cells (FIG. 9, panel B).

Figure 10:
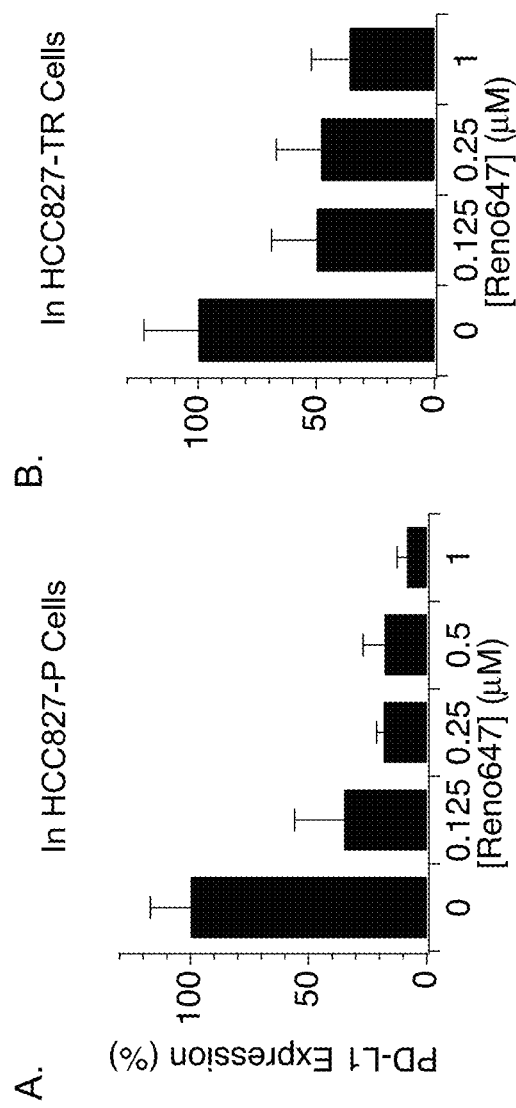
FIG. 10 depicts the effects of Reno647 on expression of PD-L1 in HCC827-P and HCC827-TR cells. HCC827-P and HCC827-TR cells at exponential growth phase were exposed to indicated concentration of Reno647 for 24 hrs. Total cellular RNA was extracted and cDNA was prepared followed by qRT-PCR using specific probes for PD-L1 and GAPDH (internal control) as described in the section of Materials and Methods. Tgene ΔCt value was normalized for GAPDH by calculating ΔCt=Ctgene−CtGAPDH per sample.

It is interestingly noted that Renotinibs significantly inhibited expression of PD-L1 in both HCC827-P and HCC826-TR cells (expression of PD-L1 in HCC827-0R16 is lost by an unknown mechanism that is currently under investigation). The suppression of PD-L1 expression by Reno647 was found to be concentration-dependent. An example of Reno647 on expression of PD-L1 by qRT-PCR in both HCC827-P and HCC826-TR cells is shown in FIG. 10. Over 93% reduction of PD-L1 expression was observed when the HCC827-P cells were treated with 1 µM of Reno647. This observation suggests that Renotinibs may potentially activate host immune response in vivo that in turn will enhance anti-cancer activity of these compounds against PD-L1 positive cancer cells.

REFERENCES

Bean, J., C. Brennan, et al. (2007). "MET amplification occurs with or without T790M mutations in EGFR mutant lung tumors with acquired resistance to gefitinib or erlotinib." *Proc Natl Acad Sci USA* 104(52): 20932-20937.

Chou, T. C., R. J. Motzer, et al. (1994). "Computerized quantitation of synergism and antagonism of taxol, topotecan, and cisplatin against human teratocarcinoma cell growth: a rational approach to clinical protocol design." *J Natl Cancer Inst* 86(20): 1517-1524.

Christoffersen, T., T. K. Guren, et al. (2009). "Cancer therapy targeted at cellular signal transduction mechanisms: strategies, clinical results, and unresolved issues." *Eur J Pharmacol* 625(1-3): 6-22.

de Bruin, E. C., C. Cowell, et al. (2014). "Reduced NF1 expression confers resistance to EGFR inhibition in lung cancer." *Cancer Discov* 4(5): 606-619.

Eberlein, C. A., D. Stetson, et al. (2015). "Acquired Resistance to the Mutant-Selective EGFR Inhibitor AZD9291 Is Associated with Increased Dependence on RAS Signaling in Preclinical Models." *Cancer Res* 75(12): 2489-2500.

Engelman, J. A., K. Zejnullahu, et al. (2007). "MET amplification leads to gefitinib resistance in lung cancer by activating ERBB3 signaling." *Science* 316(5827): 1039-1043.

Eskens, F. A., C. H. Mom, et al. (2008). "A phase I dose escalation study of BIBW 2992, an irreversible dual inhibitor of epidermal growth factor receptor 1 (EGFR) and 2 (HER2) tyrosine kinase in a 2-week on, 2-week off schedule in patients with advanced solid tumours." *Br J Cancer* 98(1): 80-85.

Gatzemeier, U., A. Pluzanska, et al. (2007). "Phase III study of erlotinib in combination with cisplatin and gemcitabine in advanced non-small-cell lung cancer: the Tarceva Lung Cancer Investigation Trial." *J Clin Oncol* 25(12): 1545-1552.

Graus-Porta, D., R. R. Beerli, et al. (1997). "ErbB-2, the preferred heterodimerization partner of all ErbB receptors, is a mediator of lateral signaling." *Embo J* 16(7): 1647-1655.

Herbst, R. S., D. Prager, et al. (2005). "TRIBUTE: a phase III trial of erlotinib hydrochloride (OSI-774) combined with carboplatin and paclitaxel chemotherapy in advanced non-small-cell lung cancer." *J Clin Oncol* 23(25): 5892-5899.

Herbst, R. S. and D. M. Shin (2002). "Monoclonal antibodies to target epidermal growth factor receptor-positive tumors: a new paradigm for cancer therapy." *Cancer* 94(5): 1593-1611.

Higashiyama, S., J. A. Abraham, et al. (1991). "A heparin-binding growth factor secreted by macrophage-like cells that is related to EGF." *Science* 251(4996): 936-939.

Hynes, N. E. and H. A. Lane (2005). "ERBB receptors and cancer: the complexity of targeted inhibitors." *Nat Rev Cancer* 5(5): 341-354.

Hynes, N. E. and G. MacDonald (2009). "ErbB receptors and signaling pathways in cancer." *Curr Opin Cell Biol* 21(2): 177-184.

Jester, B. W., K. J. Cox, et al. (2010). "A coiled-coil enabled split-luciferase three-hybrid system: applied toward profiling inhibitors of protein kinases." *J Am Chem Soc* 132(33): 11727-11735.

Jester, B. W., A. Gaj, et al. (2012). "Testing the promiscuity of commercial kinase inhibitors against the AGC kinase group using a split-luciferase screen." *J Med Chem* 55(4): 1526-1537.

Katakami, N., S. Atagi, et al. (2013). "LUX-Lung 4: a phase II trial of afatinib in patients with advanced non-small-cell lung cancer who progressed during prior treatment with erlotinib, gefitinib, or both." *J Clin Oncol* 31(27): 3335-3341.

Kataoka, H. (2009). "EGFR ligands and their signaling scissors, ADAMs, as new molecular targets for anticancer treatments." *J Dermatol Sci* 56(3): 148-153.

Kim, S. M., J. S. Kim, et al. (2010). "Acquired resistance to cetuximab is mediated by increased PTEN instability and leads cross-resistance to gefitinib in HCC827 NSCLC cells." *Cancer Lett* 296(2): 150-159.

Kobayashi, S., T. J. Boggon, et al. (2005). "EGFR mutation and resistance of non-small-cell lung cancer to gefitinib." *N Engl J Med* 352(8): 786-792.

Lee, M. S., H. P. Kim, et al. (2012). "Gefitinib resistance of cancer cells correlated with TM4SF5-mediated epithelial-mesenchymal transition." *Biochim Biophys Acta* 1823(2): 514-523.

Li, N., L. Feng, et al. (2016). "PARP Inhibition Suppresses Growth of EGFR-Mutant Cancers by Targeting Nuclear PKM2." *Cell Rep.*

Madison, D. L., D. Stauffer, et al. (2011). "The PARP inhibitor PJ34 causes a PARP1-independent, p21 dependent mitotic arrest." *DNA Repair (Amst)* 10(10): 1003-1013.

Mencher, S. K. and L. G. Wang (2005). "Promiscuous drugs compared to selective drugs (promiscuity can be a virtue)." *BMC Clin Pharmacol* 5(1): 3.

Miller, V. A., V. Hirsh, et al. (2012). "Afatinib versus placebo for patients with advanced, metastatic non-small-cell lung cancer after failure of erlotinib, gefitinib, or both, and one or two lines of chemotherapy (LUX-Lung 1): a phase 2b/3 randomised trial." *Lancet Oncol* 13(5): 528-538.

Mitsudomi, T., T. Kosaka, et al. (2006). "Biological and clinical implications of EGFR mutations in lung cancer." *Int J Clin Oncol* 11(3): 190-198.

Mok, T. S., Y. L. Wu, et al. (2009). "Gefitinib or carboplatin-paclitaxel in pulmonary adenocarcinoma." *N Engl J Med* 361(10): 947-957.

Ohashi, K., L. V. Sequist, et al. (2012). "Lung cancers with acquired resistance to EGFR inhibitors occasionally harbor BRAF gene mutations but lack mutations in KRAS, NRAS, or MEK1." *Proc Natl Acad Sci USA* 109(31): E2127-2133.

Park, W. H., C. W. Jung, et al. (2003). "Trichostatin inhibits the growth of ACHN renal cell carcinoma cells via cell cycle arrest in association with p27, or apoptosis." *Int J Oncol* 22(5): 1129-1134.

Qiu, L., W. Di, et al. (2005). "Targeted inhibition of transient activation of the EGFR-mediated cell survival pathway enhances paclitaxel-induced ovarian cancer cell death." *Int J Oncol* 27(5): 1441-1448.

Qiu, W., R. Lam, et al. (2014). "Insights into the binding of PARP inhibitors to the catalytic domain of human tankyrase-2." *Acta Crystallogr D Biol Crystallogr* 70(Pt 10): 2740-2753.

Rosell, R., E. Carcereny, et al. (2012). "Erlotinib versus standard chemotherapy as first-line treatment for European patients with advanced EGFR mutation-positive non-small-cell lung cancer (EURTAC): a multicentre, open-label, randomised phase 3 trial." *Lancet Oncol* 13(3): 239-246.

Rosell, R., T. Moran, et al. (2009). "Screening for epidermal growth factor receptor mutations in lung cancer." *N Engl J Med* 361(10): 958-967.

Skehan, P., R. Storeng, et al. (1990). "New colorimetric cytotoxicity assay for anticancer-drug screening." *J Natl Cancer Inst* 82(13): 1107-1112.

Solomon, B., J. Hagekyriakou, et al. (2003). "EGFR blockade with ZD1839 ('Iressa') potentiates the antitumor effects of single and multiple fractions of ionizing radiation in human A431 squamous cell carcinoma. Epidermal growth factor receptor." *Int J Radiat Oncol Biol Phys* 55(3): 713-723.

Sos, M. L., H. B. Rode, et al. (2010). "Chemogenomic profiling provides insights into the limited activity of irreversible EGFR Inhibitors in tumor cells expressing the T790M EGFR resistance mutation." *Cancer Res* 70(3): 868-874.

Sramkoski, R. M., T. G. Pretlow, 2nd, et al. (1999). "A new human prostate carcinoma cell line, 22Rv1." In *Vitro Cell Dev Biol Anim* 35(7): 403-409.

Takeuchi, K. and F. Ito (2010). "EGF receptor in relation to tumor development: molecular basis of responsiveness of cancer cells to EGFR-targeting tyrosine kinase inhibitors." *Febs J* 277(2): 316-326.

Takezawa, K., V. Pirazzoli, et al. (2012). "HER2 amplification: a potential mechanism of acquired resistance to EGFR inhibition in EGFR-mutant lung cancers that lack the second-site EGFRT790M mutation." *Cancer Discov* 2(10): 922-933.

Wang, J., N. W. Pursell, et al. (2013). "Potential advantages of CUDC-101, a multitargeted HDAC, EGFR, and HER2 inhibitor, in treating drug resistance and preventing cancer cell migration and invasion." *Mol Cancer Ther* 12(6): 925-936.

Wang, J., R. Ramakrishnan, et al. (2010). "Quantifying EGFR alterations in the lung cancer genome with nanofluidic digital PCR arrays." *Clin Chem* 56(4): 623-632.

Wang, L. G., X. M. Liu, et al. (1997). "Down-regulation of prostate-specific antigen expression by finasteride through inhibition of complex formation between androgen receptor and steroid receptor-binding consensus in the promoter of the PSA gene in LNCaP cells." *Cancer Res* 57(4): 714-719.

Wang, L. G., L. Ossowski, et al. (2004). "Androgen receptor level controlled by a suppressor complex lost in an androgen-independent prostate cancer cell line." *Oncogene* 23(30): 5175-5184.

Yewale, C., D. Baradia, et al. (2013). "Epidermal growth factor receptor targeting in cancer: a review of trends and strategies." *Biomaterials* 34(34): 8690-8707.

Yu, H. and R. Jove (2004). "The STATs of cancer—new molecular targets come of age." *Nat Rev Cancer* 4(2): 97-105.

Yun, C. H., K. E. Mengwasser, et al. (2008). "The T790M mutation in EGFR kinase causes drug resistance by increasing the affinity for ATP." *Proc Natl Acad Sci USA* 105(6): 2070-2075.

What is claimed is:

1. A compound having the structure of Formula I:

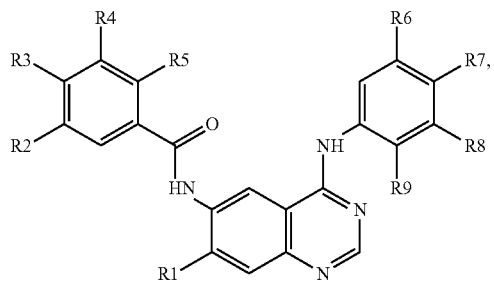

Formula I wherein: R1 is selected from the group consisting of:

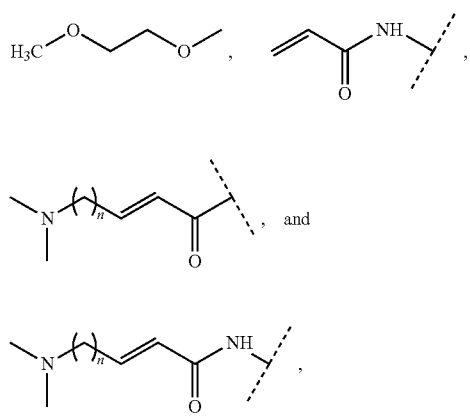

where n is 0, 1, 2, 3, or 4;
R2 is selected from the group consisting of: —H, —CH₃, —OCH₃, —NO₂ and a halogen,
R3 is selected from the group consisting of: —H, —CH₃, —OCH₃, and a halogen,
R4 is selected from the group consisting of: —H, —CH₃, —OCH₃, —NO₂, and a halogen,
R5 is selected from the group consisting of: —H, —CH₃, —OCH₃, and a halogen,
R6 is selected from the group consisting of: —H, and a halogen,
R7 is selected from the group consisting of: —H, and a halogen,
R8 is selected from the group consisting of: —H, and an ethynyl, and
R9 is selected from the group consisting of: —H, and a halogen, or a pharmaceutically acceptable salt thereof.

2. The compound of claim 1, having the structure of Formula II:

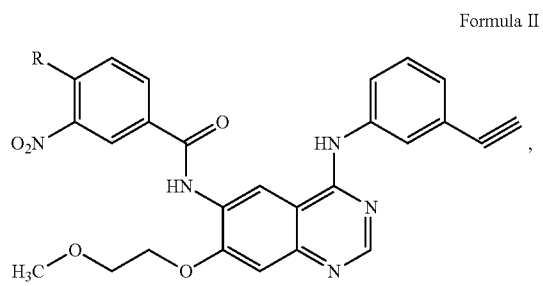

Formula II wherein R is a halogen, or the pharmaceutically acceptable salt thereof.

3. The compound or the pharmaceutically acceptable salt thereof of claim 2, wherein R is selected from the group consisting of: fluoride, chloride, and bromide.

4. The compound of claim 3, wherein R is a fluoride.

5. The compound of claim 1, having the structure of Formula III:

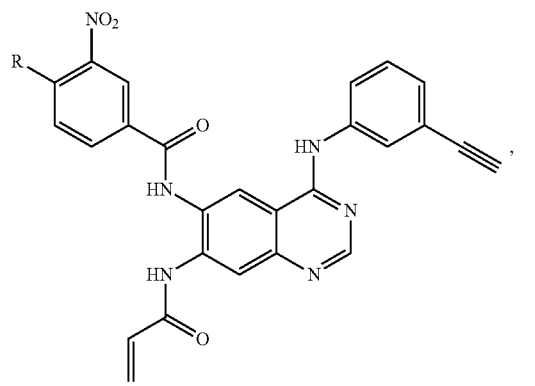

Formula III wherein R is a halogen, or the pharmaceutically acceptable salt thereof.

6. The compound or pharmaceutical acceptable salt thereof of claim 5, wherein R is selected from the group consisting of: fluoride, chloride, bromide, and iodide.

7. A pharmaceutical composition comprising:
a compound having the structure of Formula I:

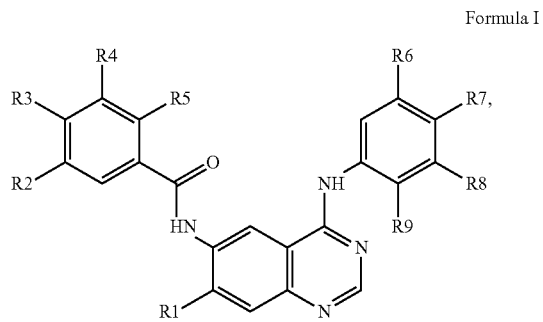

Formula I wherein: R1 is selected from the group consisting of:

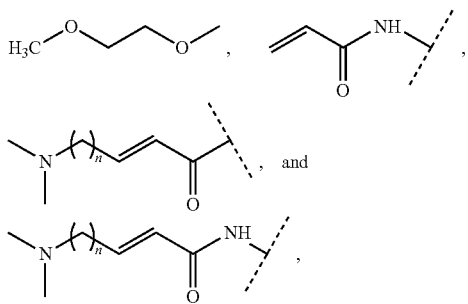

where n is 0, 1, 2, 3, or 4;
- R2 is selected from the group consisting of: —H, —CH$_3$, —OCH$_3$, and a halogen,
- R3 is selected from the group consisting of: —H, —CH$_3$, —OCH$_3$, and a halogen,
- R4 is selected from the group consisting of: —H, —CH$_3$, —OCH$_3$, —NO$_2$, and a halogen,
- R5 is selected from the group consisting of: —H, —CH$_3$, —OCH$_3$, and a halogen,
- R6 is selected from the group consisting of: —H, and a halogen,
- R7 is selected from the group consisting of: —H, and a halogen,
- R8 is selected from the group consisting of: —H, and an ethynyl, and
- R9 is selected from the group consisting of: —H, and a halogen, or a salt thereof; and
a pharmaceutically acceptable carrier.

8. The pharmaceutical composition of claim 7, further comprising at least one additional anti-cancer agent selected from the group consisting of: a conventional chemotherapeutic agent, a protein kinase inhibitor, a topoisomerase inhibitor, a mitotic kinesin inhibitor, a histone deacetylase inhibitor, a mTOR inhibitor, a growth factor inhibitor, a growth factor receptor inhibitor, a transcriptional factor inhibitor, an anticancer monoclonal antibody, and glucocorticoid hormones for the simultaneous, separate, or sequential treatment of cancer.

9. The composition of claim 8, wherein the conventional chemotherapeutic agent is selected from the group consisting of: an alkylating agent, an anti-metabolitic agent, an antibiotic, an anti-tubule agent, and an anti-hormonal agent.

10. The composition of claim 8, wherein the conventional chemotherapeutic agent is selected from the group consisting of: mechlorethamine, cyclophosphamide, Busulfan, chlorambucil, leukeran, paraplatin, cisplatin, carboplatin, platinol, Methotrexate (MTX), 6-mercaptopurine (6-MP), cytarabine (Ara-C), floxuridine (FUDR), fluorouracil, hydroxyurea (Hydrea), etoposide (VP16), actinomycin D, bleomycin, mithramycin, daunorubicin, paclitaxel, and its derivatives, *vinca* and its derivatives, bicalutamide, Flutamide, Tamoxifen, and Megestrol.

11. The composition of claim 8, wherein the protein kinase inhibitor is selected from the group consisting of: inhibitors of cyclin-dependent kinases, tyrosine kinases, phosphoinositide 3-kinase PI3K/AKT, protein kinase C, casein kinases, MAP kinases, and Src kinases.

12. The composition of claim 8, wherein the protein kinase inhibitor is selected from the group consisting of: midostaurin, 7-hydroxystaurosporine, bryostatin 1, perifosine, ilmofosine, Ro 31-8220, Ro 32-0432, GO 6976, ISIS-3521, macrocyclic bis (indolyl) maleimides, AZD9291, and erlotinib.

13. The composition of claim 8, wherein the anticancer monoclonal antibody is selected from the group consisting of: Cetuximab, Herceptin, and Bevacizumab.

14. The composition of claim 8, wherein the glucocorticoid hormone is selected from the group consisting of: dexamethasone, prednisone, prednisolone, metyylprednisolone, and hydrocoritisone.

* * * * *